(12) United States Patent
Rangachari et al.

(10) Patent No.: US 7,771,494 B2
(45) Date of Patent: Aug. 10, 2010

(54) PROCESS FOR SELECTIVE REMOVAL OF WATER AND IMPURITIES FROM N-(PHOSPHONOMETHYL)GLYCINE

(75) Inventors: Sunder Rangachari, Ballwin, MO (US); Ed Ries, Kirkwood, MO (US); Eduardo Casanova, University City, MO (US); Randall Alberts, LaPlace, LA (US); Todd Friedman, Imperial, MO (US); Greg Hartmann, Kirkwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 515 days.

(21) Appl. No.: 11/669,693

(22) Filed: Jan. 31, 2007

(65) Prior Publication Data

US 2008/0178433 A1    Jul. 31, 2008

(51) Int. Cl.
*B01D 9/00* (2006.01)
(52) U.S. Cl. .......................... 23/295 R; 23/296; 23/304
(58) Field of Classification Search ............... 23/295 R, 23/296, 304
See application file for complete search history.

(56) References Cited

U.S. PATENT DOCUMENTS

| | | |
|---|---|---|
| 3,799,758 A | 3/1974 | Franz |
| 3,950,402 A | 4/1976 | Franz |
| 3,969,398 A | 7/1976 | Hershman |
| 4,582,650 A | 4/1986 | Felthouse |
| 4,624,937 A | 11/1986 | Chou |
| 4,696,772 A | 9/1987 | Chou |
| 5,179,228 A | 1/1993 | Ramon et al. |
| 6,417,133 B1 | 7/2002 | Ebner et al. |
| 6,586,621 B2 | 7/2003 | Leiber et al. |
| 6,730,813 B2 | 5/2004 | Hitzler et al. |
| 7,015,351 B2 | 3/2006 | Haupfear et al. |
| 7,071,354 B2 | 7/2006 | Vandenmersch et al. |
| 2002/0068836 A1 | 6/2002 | Haupfear et al. |
| 2004/0010160 A1 | 1/2004 | Coleman et al. |
| 2004/0235664 A1 | 11/2004 | Vandenmersch et al. |
| 2005/0035060 A1 | 2/2005 | Vigil et al. |
| 2005/0059840 A1 | 3/2005 | Haupfear et al. |

FOREIGN PATENT DOCUMENTS

| | | |
|---|---|---|
| CN | 1775786 A | 5/2006 |
| CN | 1827626 A | 9/2006 |
| CN | 1843587 A | 10/2006 |
| CN | 101007822 | 8/2007 |
| IN | 2003DE01223 A | 5/2005 |
| IT | 01281094 | 2/1998 |
| WO | 00/01707 A1 | 1/2000 |
| WO | 00/09517 A2 | 2/2000 |
| WO | 0160830 A1 | 8/2001 |
| WO | 2005/016519 A1 | 2/2005 |
| WO | 2006/031938 A2 | 3/2006 |
| WO | 2006/089193 A2 | 8/2006 |

OTHER PUBLICATIONS

International Search Report issued in connection with PCT/US2008/052482, dated May 14, 2008, 4 Pages.
Franz, J. E., et al., Glyphosate: A Unique Global Herbicide, Chapter 8—Methods of Preparing Glyphosate, American Chemical Society, 1997 pp. 233-262, Washington, D.C.
Porter, M.C., Section 2.1—Membrane Filtration, pp. 2-4-2-103.
Tanninen, J., et al., "Long-Term Acid Resistance and Selectivity of NF Membranes in Very Acidic Conditions," Journal of Membrane Science, 2004, pp. 11-18, vol. 240.
Tanninen, J., et al., "Nanofiltration of Sulphuric Acid from Metal Sulphate Solutions," Proceedings of IMSTEC '03, Nov. 10-14, 2003, pp. 1-6, Sydney, Australia.

*Primary Examiner*—Edward M Johnson
(74) *Attorney, Agent, or Firm*—Senniger Powers LLP; Joseph A. Schaper

(57) ABSTRACT

Processes for the preparation, concentration and recovery an N-(phosphonomethyl)glycine product from aqueous process streams including contacting mother liquor generated in the precipitation of N-(phosphonomethyl)glycine product crystals with a selective membrane to produce a retentate enriched N-(phosphonomethyl)glycine product and a permeate depleted in N-(phosphonomethyl)glycine product are disclosed.

29 Claims, 7 Drawing Sheets

PROCESS FOR SELECTIVE REMOVAL OF WATER AND IMPURITIES FROM N-(PHOSPHONOMETHYL)GLYCINE

FIELD OF THE INVENTION

The present invention relates generally to processes that utilize selective membrane separation techniques in the production and recovery of an N-(phosphonomethyl)glycine product from aqueous process streams, in particular aqueous process slurries comprising N-(phosphonomethyl)glycine product crystals and a mother liquor.

BACKGROUND OF THE INVENTION

N-(phosphonomethyl)glycine (glyphosate) is described by Franz in U.S. Pat. No. 3,799,758. N-(phosphonomethyl)glycine and its salts are conveniently applied as a component of aqueous, post-emergent herbicide formulations. As such, they are particularly useful as a highly effective and commercially important broad-spectrum herbicide for killing or controlling the growth of a wide variety of plants, including germinating seeds, emerging seedlings, maturing and established woody and herbaceous vegetation and aquatic plants.

One of the more widely accepted methods of making N-(phosphonomethyl)glycine products includes the catalyzed liquid phase oxidative cleavage of a carboxymethyl substituent from an N-(phosphonomethyl)iminodiacetic acid (PMIDA) substrate. Over the years, a wide variety of methods and reactor systems have been disclosed for conducting this oxidation reaction. See generally, Franz, et al., Glyphosate: A Unique Global Herbicide (ACS Monograph 189, 1997) at pp. 233-62 (and references cited therein); Franz, U.S. Pat. No. 3,950,402; Hershman, U.S. Pat. No. 3,969,398; Felthouse, U.S. Pat. No. 4,582,650; Chou, U.S. Pat. No. 4,624,937; Chou, U.S. Pat. No. 4,696,772; Ramon et al., U.S. Pat. No. 5,179,228; Siebenhaar et al., International Publication No. WO 00/01707; Ebner et al., U.S. Pat. No. 6,417,133; Leiber et al., U.S. Pat. No. 6,586,621; and Haupfear et al., U.S. Pat. No. 7,015,351.

For example, such reaction may be conducted in either a batch or continuous oxidation reactor system in the presence of a catalyst that typically comprises particulate carbon, or a noble metal such as platinum on a particulate carbon support. The catalyst is usually slurried in an aqueous solution of PMIDA within a stirred tank reactor, and molecular oxygen introduced into the reactor to serve as the oxidizing agent. The reaction is exothermic. The liquid phase oxidation of a PMIDA substrate typically produces a reaction mixture containing water and various impurities besides the desired N-(phosphonomethyl)glycine product. These impurities may include, for example, various by-products, unreacted starting materials, as well as impurities present in the starting materials. Representative examples of impurities present in N-(phosphonomethyl)glycine product reaction mixtures include unreacted PMIDA substrate, N-formyl-N-(phosphonomethyl)glycine, phosphoric acid, phosphorous acid, hexamethylenetetraamine, aminomethylphosphonic acid (AMPA), methyl aminomethylphosphonic acid (MAMPA), iminodiacetic acid (IDA), formaldehyde, formic acid, chlorides and the like.

Commercial considerations sometimes dictate that the concentration of the N-(phosphonomethyl)glycine product in the commercially sold mixtures be significantly greater than the concentrations in the reaction mixtures that are typically formed in the oxidation reactor system, particularly where the N-(phosphonomethyl)glycine product is being stored or shipped for agricultural applications. For example, when a heterogeneous catalyst is used for the liquid phase oxidation of PMIDA to make N-(phosphonomethyl)glycine as described by Haupfear et al. in U.S. Pat. No. 7,015,351, it is typically preferred to maintain a maximum concentration of the N-(phosphonomethyl)glycine product in the reaction mixture of no greater than about 9% by weight in order to keep the product solubilized, although higher concentrations in excess of 9% and even up to about 12% by weight may be suitably utilized at higher reaction mixture temperatures. Sometimes, however, it is desirable for the commercially sold mixtures to have an N-(phosphonomethyl)glycine concentration that is significantly greater. Thus, after the N-(phosphonomethyl)glycine product has been formed and, if necessary, separated from the catalyst, it is often preferred to concentrate the product and separate the product from the various impurities in the oxidation reaction mixture.

Concentration of the glyphosate product typically comprises one or more crystallization steps. The value of the N-(phosphonomethyl)glycine product normally dictates maximal recovery of the product from the reaction mixture and also often provides incentive for recycling at least a portion of the depleted reaction mixture (i.e., crystallization mother liquor). The mother liquor stream or streams obtained in the crystallization may be recycled to crystallization or reaction steps of the process. A fraction of the mother liquor(s) is generally removed from the process in order to purge by-products and control the purity of the N-(phosphonomethyl)glycine product. The crystallized N-(phosphonomethyl)glycine product may be dried and sold as a solid crystalline product. A substantial fraction of the glyphosate crystals are commonly neutralized with a base such as isopropylamine, KOH, etc. in an aqueous medium to produce a concentrated salt solution. A concentrated formulation comprising the glyphosate salt solution, and often also other components such as, for example, various surfactants, is a principal product of commerce.

Haupfear et al., in U.S. Pat. No. 7,015,351, describe various processes for purifying and concentrating an N-(phosphonomethyl)glycine product solution prepared by the oxidation of a PMIDA substrate. Haupfear et al. disclose generating two crystalline N-(phosphonomethyl)glycine products (i.e., wet-cakes) in two separate crystallizer trains operated in semi-parallel, one train including an adiabatic crystallizer and the other including a heat-driven evaporative crystallizer. The wet-cake products have distinct impurity profiles and the lower purity material issuing from the heat-driven evaporative crystallizer train may be combined with the higher purity material issuing from the adiabatic crystallizer train to produce a single product of acceptable purity.

Donadello, in Italian Patent No. 1281094, describes a process for removal of formaldehyde from N-(phosphonomethyl)glycine reaction mixtures comprising N-(phosphonomethyl)glycine or salts thereof and produced by the catalytic oxidation of N-(phosphonomethyl)iminodiacetic acid or salts thereof. In one embodiment, mother liquor from the crystallization of the N-(phosphonomethyl)glycine reaction mixture is subjected to selective membrane separation utilizing a reverse osmosis or nanofiltration membrane to produce a permeate containing formaldehyde and a concentrate or retentate enriched in N-(phosphonomethyl)glycine. The retentate can be subjected to crystallization to recover residual N-(phosphonomethyl)glycine and the resulting mother liquor recycled to the selective membrane separation step.

Vandenmersch et al., in U.S. Pat. No. 7,071,354, describe a process for recovery of N-(phosphonomethyl)glycine from aqueous mixtures containing N-(phosphonomethyl)glycine, ammonium halides and alkali metal or alkaline earth metal halides. Rather than oxidation of an N-(phosphonomethyl) iminodiacetic acid substrate, the aqueous mixture preferably originates from the reaction of a hexahydrotriazine derivative and a triacyl phosphite and is obtained after precipitation and recovery of the N-(phosphonomethyl)glycine product. The process includes adjusting the pH of the aqueous mixture from 2 to 8 and subjecting the mixture to a separation on a selective nanofiltration membrane to produce a retentate and a permeate said to be enriched in N-(phosphonomethyl)glycine and halides, respectively. Depending on its concentration and purity, the retentate can optionally be concentrated (e.g., by distillation or reverse osmosis) to obtain N-(phosphonomethyl)glycine in crystalline form that can be recovered in a customary manner, such as by filtration.

Vigil et al., in U.S. Publication No. U.S. 2005/0035060 A1 disclose a process for removing formaldehyde and formic acid impurities from N-(phosphonomethyl)glycine reaction solutions originating from the oxidation of N-(phosphonomethyl)iminodiacetic acid. The process includes providing a N-(phosphonomethyl)glycine solution containing between 0.1% and 3% w/v N-(phosphonomethyl)glycine, 0.5% to 1% w/v formaldehyde, and 0.1% to 0.6% formic acid; adjusting the pH of the initial N-(phosphonomethyl)glycine solution to between 2.5 and 3.5 with a base such as alkylamine, ammonium hydroxide, sodium or potassium hydroxide; contacting the solution with a nanofiltration membrane at a temperature between 10° C. and 35° C. and a pressure between 25 and 35 kg/cm$^2$; recycling the retentate solution to the nanofiltration membrane; and discarding the permeate solution containing the impurities. After successive recycling, a glyphosate concentration of up to approximately 8% is obtained in the recovered retentate solution.

There remains a need for improved processes for concentrating and purifying N-(phosphonomethyl)glycine product in aqueous process streams that utilize selective membrane separation techniques. There is particular need for such processes capable of reducing the operating costs associated with concentrating and precipitating the N-(phosphonomethyl) glycine product and which effectively use selective membrane separation to maximize recovery of the product from aqueous process slurries comprising N-(phosphonomethyl) glycine product crystals and a mother liquor.

SUMMARY OF THE INVENTION

Briefly, therefore, the present invention is directed to processes for the preparation, concentration and recovery of an N-(phosphonomethyl)glycine product from aqueous process streams. In accordance with certain embodiments, the process generally comprises oxidizing an N-(phosphonomethyl) iminodiacetic acid substrate in an oxidation reaction zone to produce an aqueous oxidation reaction solution comprising N-(phosphonomethyl)glycine product. N-(phosphonomethyl)glycine product crystals are precipitated from the aqueous oxidation reaction solution to produce an aqueous product slurry comprising precipitated N-(phosphonomethyl) glycine product crystals and mother liquor saturated or supersaturated in N-(phosphonomethyl)glycine product. At least a portion of the aqueous product slurry is separated into a solids-enriched slurry fraction comprising N-(phosphonomethyl)glycine product crystals and a solids-depleted mother liquor fraction. The solids-depleted mother liquor fraction is contacted with a selective membrane to produce a retentate enriched in N-(phosphonomethyl)glycine product relative to the solids-depleted mother liquor fraction and a permeate depleted in N-(phosphonomethyl)glycine product relative to the solids-depleted mother liquor fraction. N-(phosphonomethyl)glycine product crystals are precipitated from the retentate. In accordance with one embodiment, the solids-depleted mother liquor fraction initially contacted with the selective membrane is saturated or supersaturated in N-(phosphonomethyl)glycine product.

In another embodiment of the present invention, precipitation of N-(phosphonomethyl)glycine product crystals from the aqueous oxidation reaction solution to generate a mother liquor for selective membrane treatment is achieved by increasing the concentration of N-(phosphonomethyl)glycine product by removal of water from the aqueous oxidation reaction solution. In accordance with a preferred embodiment, the aqueous oxidation reaction solution is cooled as water is evaporated from the aqueous oxidation reaction solution under substantially adiabatic conditions by reducing the pressure to thereby increase the concentration of N-(phosphonomethyl)glycine product in the aqueous oxidation reaction solution, precipitate N-(phosphonomethyl)glycine product crystals and produce the aqueous product slurry comprising precipitated N-(phosphonomethyl)glycine product crystals and the mother liquor.

In a still further embodiment of the present invention, at least a portion of the permeate is recycled and introduced into the oxidation reaction zone.

The present invention is also directed to processes for recovering an N-(phosphonomethyl)glycine product from an aqueous product slurry comprising N-(phosphonomethyl) glycine product crystals and a mother liquor. In a first embodiment, the process comprises first separating at least a portion of the aqueous product slurry into a solids-enriched slurry fraction comprising N-(phosphonomethyl)glycine product crystals and a solids-depleted mother liquor fraction comprising N-(phosphonomethyl)glycine. N-(phosphonomethyl)glycine product crystals are separated from the solids-enriched slurry fraction to produce an N-(phosphonomethyl) glycine wet-cake product and the solids-depleted mother liquor fraction is contacted with a selective membrane to produce a retentate enriched in N-(phosphonomethyl)glycine relative to the solids-depleted mother liquor fraction and a permeate depleted in N-(phosphonomethyl)glycine relative to the solids-depleted mother liquor fraction. N-(phosphonomethyl)glycine product crystals are precipitated from the retentate and at least a portion of the permeate is recycled and combined with the solids-depleted mother liquor fraction to dilute and reduce the concentration of N-(phosphonomethyl) glycine in the solids-depleted mother liquor fraction contacted with the selective membrane.

In another embodiment, the process comprises decanting a solids-depleted mother liquor decantate comprising N-(phosphonomethyl)glycine from at least a portion of the aqueous product slurry to form a solids-enriched slurry fraction comprising N-(phosphonomethyl)glycine product crystals. N-(phosphonomethyl)glycine product crystals are separated from the solids-enriched slurry fraction to produce an N-(phosphonomethyl)glycine wet-cake product and the solids-depleted mother liquor decantate is contacted with a selective membrane to produce a retentate enriched in N-(phosphonomethyl)glycine relative to the solids-depleted mother liquor decantate and a permeate depleted in N-(phosphonomethyl)glycine relative to the solids-depleted mother liquor decantate. N-(phosphonomethyl)glycine product crystals are precipitated from the retentate.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Improved processes for producing and recovering N-(phosphonomethyl)glycine product from aqueous product slurries comprising N-(phosphonomethyl)glycine product crystals and a mother liquor have been devised. The present invention utilizes selective membrane separation to treat aqueous process streams such as the solids-depleted mother liquor comprising N-(phosphonomethyl)glycine product resulting from concentrating and purifying an N-(phosphonomethyl)glycine product solution prepared by the oxidation of a PMIDA substrate. The processes disclosed herein may be employed to reduce the operating costs and energy requirements associated with concentrating and precipitating the N-(phosphonomethyl)glycine product, while providing a high degree of product recovery.

The present invention has particular application in the concentration and recovery of N-(phosphonomethyl)glycine product from oxidation reaction solutions produced by the catalytic liquid phase oxidation of a PMIDA substrate. As used herein, "N-(phosphonomethyl)iminodiacetic acid or PMIDA substrates" include N-(phosphonomethyl)iminodiacetic acid and salts thereof, wherein the salt-forming cation is, for example, ammonium, alkylammonium, alkali metal or other agronomically acceptable cations. Although the following disclosure focuses on the recovery of N-(phosphonomethyl)glycine product from the catalytic liquid phase oxidation of a PMIDA substrate, it should be understood that the present invention is also generally applicable to recovering N-(phosphonomethyl)glycine product produced by other routes known to those skilled in the art.

Oxidation Reactor System

Figure 1:
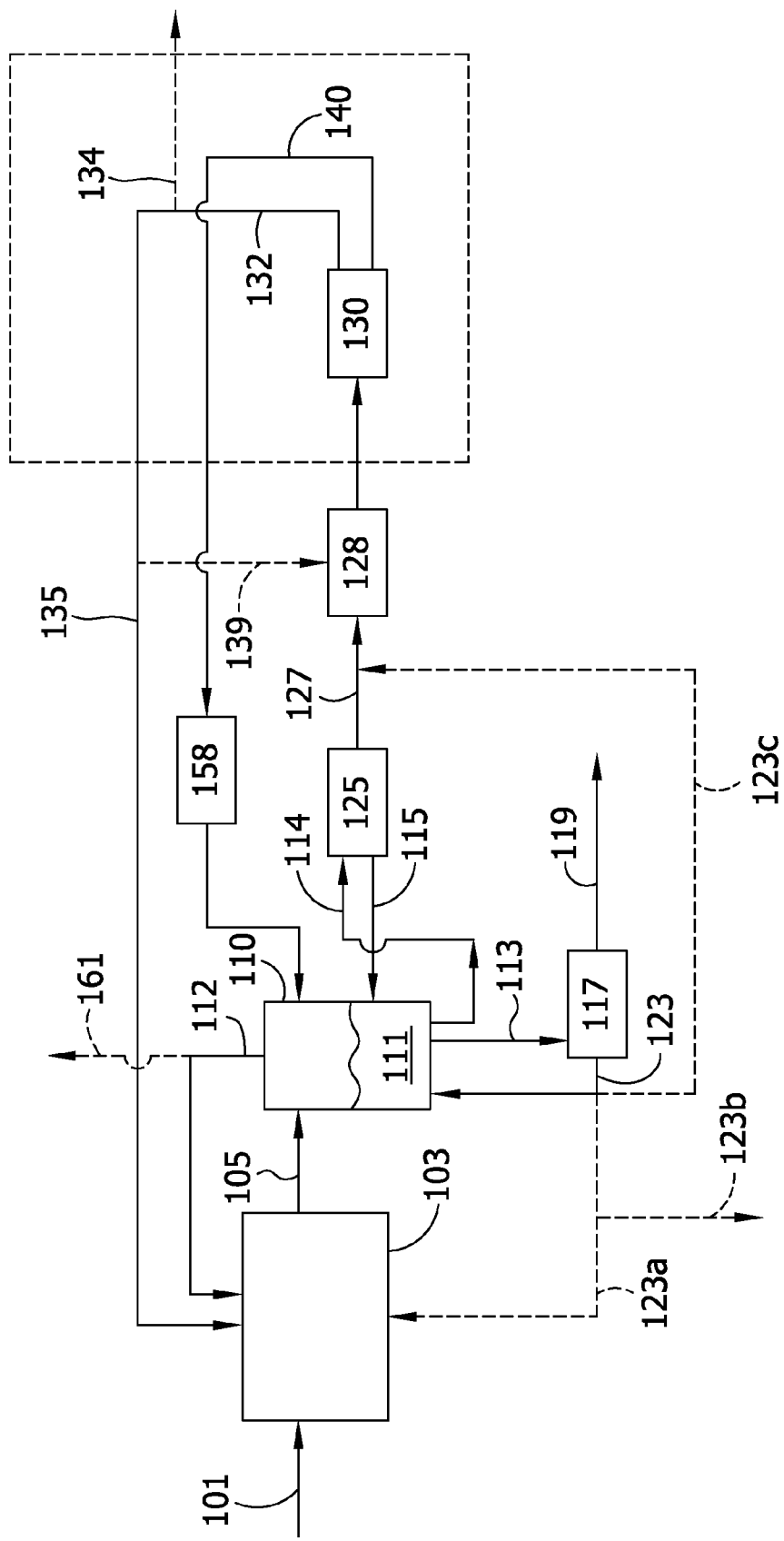
FIG. 1 is a schematic flow sheet of a process for oxidizing an N-(phosphonomethyl)iminodiacetic acid substrate in an oxidation reactor system, forming an aqueous product slurry comprising N-(phosphonomethyl)glycine product crystals and a mother liquor and recovering an N-(phosphonomethyl)glycine product from the aqueous product slurry utilizing a selective membrane system in which a solids-depleted mother liquor fraction is contacted with a selective membrane.

Referring now to FIG. 1, an aqueous feed stream or slurry 101 comprising a PMIDA substrate is introduced along with an oxidizing agent into an oxidation reactor system 103. The aqueous feed stream typically comprises from about 6.5% to about 11% by weight PMIDA. The oxidation reactor system comprises one or more oxidation reaction zone(s), wherein the N-(phosphonomethyl)iminodiacetic acid substrate is oxidatively cleaved in the presence of a suitable catalyst to form an aqueous oxidation reaction solution 105 comprising N-(phosphonomethyl)glycine product and various impurities.

The liquid phase oxidation of PMIDA substrates may be carried out in an oxidation reactor system containing one or more oxidation reaction zones and operated in a batch, semi-batch or continuous mode. The oxidation reaction zone(s) may be suitably provided by various reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics. Conventionally, the oxidation reaction is conducted in one or more stirred tank reactors wherein the catalyst is slurried in an aqueous solution of PMIDA. Where the reaction is conducted in a continuous mode, the aqueous reaction medium may be caused to flow through a plurality of continuous stirred tank reactors (CSTRs) in series or through one or more fixed bed reactors comprising a catalyst for the oxidation reaction. The oxidation reactor system may include a catalyst filter to remove a particulate catalyst slurried or suspended in the reaction medium for recycle to the reactor system. In FIG. 1, details of the oxidation reactor system, including catalyst separation and recycle mechanisms (e.g., catalyst filters, catalyst holding tanks, pre-filter flash tanks and the like) that may be present have been omitted, it being understood that the oxidation reaction solution withdrawn from the reactor system has been substantially freed of catalyst, as necessary, depending on the specific reactor configuration(s) employed.

The catalyst employed may be, for example, a particulate activated carbon as described in Chou U.S. Pat. No. 4,624,937, or a transition metal/nitrogen composition on carbon as described in U.S. Application Publication No. US 2004/0010160 A1; International Publication No. WO 2005/016519 A1; and International Publication No. WO 2006/089193. In order to reduce the impurity level in the oxidation reaction solution 105, the catalyst employed in the oxidation reaction zone(s) is preferably a heterogeneous catalyst comprising a noble metal on a particulate carbon support, for example, as described by Ebner et al. in U.S. Pat. No. 6,417,133 and by Wan et al. in International Publication No. WO 2006/031938 A3. Where a particulate noble metal catalyst is used, it is typically slurried in the aqueous reaction medium at a concentration of from about 0.5% to about 5% by weight.

The oxidizing agent is preferably molecular oxygen (e.g., air, oxygen-enriched air or substantially pure oxygen), though other oxidants such as, for example, hydrogen peroxide or ozone, may also be used. Where the oxidant is molecular oxygen, it may be introduced independently into one or more, preferably all, of the oxidation reaction zones, for example, by sparging into the aqueous reaction medium. Typically, when the oxidation reaction is conducted in one or more stirred tank reactors, the oxygen pressure may be in the range of about 205 to about 2170 kPa absolute, more typically in the range of about 375 to about 1130 kPa absolute The temperature in each reaction zone of the oxidation reactor system may be independently controlled, but typically each reaction zone is operated in substantially the same temperature range as the other(s). Preferably, the temperature is controlled at a level that maintains glyphosate in solution and achieves substantial oxidation of by-product formaldehyde and formic acid, without excessive formation of either by-product iminodiacetic acid (IDA), which typically results from oxidation of PMIDA, or by-product aminomethylphosphonic acid (AMPA), which typically results from oxidation of glyphosate. Where molecular oxygen is used in a heterogeneous catalyzed reaction, the reaction is conveniently conducted at a temperature in the range from about 70° C. to about 140° C., more typically in the range from about 80° C. to about 120° C., and preferably in the range of from about 95° C. to about 105° C. Temperature within the reaction zone is conventionally controlled, for example, by transfer of heat from the reaction mixture to a cooling fluid in an indirect heat exchanger. For example, the heat exchanger may comprise coils immersed in the reaction mixture within a stirred tank reactor, a jacket on the exterior of the reactor, or an external heat exchanger through which the reaction mixture is circulated from the reactor.

The configuration of the oxidation reactor system, including the number of oxidation reaction zones and the oxidation reaction conditions are not critical in the practice of the present invention. Suitable oxidation reactor systems, oxidation reaction conditions and catalysts for liquid phase catalytic oxidation of a PMIDA substrate are well-known in the art and described, for example, by Ebner et al., in U.S. Pat. No. 6,417,133, by Leiber et al., in U.S. Pat. No. 6,586,621, by Haupfear et al., in U.S. Pat. No. 7,015,351, and by Wan et al. in International Publication No. WO 2006/031938 A3, the entire disclosures of which are incorporated herein by reference. Thus, application of the present invention is not limited to any particular configuration or mode of operation of the oxidation reactor system used to oxidize the PMIDA substrate and produce the aqueous reaction solution comprising the N-(phosphonomethyl)glycine product. As will be apparent to those skilled in the art, the strategies set forth herein may be advantageously applied in recovering N-(phosphonomethyl)glycine product from oxidation reaction solutions produced in a wide variety of oxidation reactor systems.

Crystallizing and Precipitating the N-(phosphonomethyl) glycine Product

The aqueous oxidation reaction solution 105 exiting the oxidation reactor system 103, and previously filtered as necessary to remove any oxidation catalyst suspended therein, comprises N-(phosphonomethyl)glycine product and various impurities as noted above. Typically, the maximum concentration of the N-(phosphonomethyl)glycine product in the reaction solution is no greater than about 9% by weight so that it will remain solubilized at the preferred operating temperatures. In order to recover a more concentrated glyphosate product, the reaction solution is introduced into a crystallizer 110 wherein N-(phosphonomethyl)glycine product crystals are precipitated from the aqueous oxidation reaction solution to produce an aqueous product slurry 111 comprising precipitated N-(phosphonomethyl)glycine product crystals and mother liquor and a crystallizer overhead vapor stream 112 discharged from the top of the crystallizer. Preferably, the crystallization operation comprises removal (i.e., evaporation) of water from the aqueous oxidation reaction solution to thereby increase the concentration of N-(phosphonomethyl) glycine product and precipitate N-(phosphonomethyl)glycine product crystals from the solution. Evaporative crystallization is particularly advantageous because it also removes a substantial fraction of small molecule impurities, most notably formaldehyde and formic acid, which tend to evaporate from the reaction mixture along with water as part of the crystallizer overhead vapor stream 112. For example, crystallizer 110 may comprise a non-adiabatic heat-driven evaporative crystallizer in which the crystallization operation comprises the addition of heat to the aqueous oxidation reaction solution to evaporate water and thereby concentrate and crystallize the N-(phosphonomethyl)glycine product. However, in order to realize the benefits of subsequent selective membrane separation operations in reducing energy requirements associated with removing water and concentrating the N-(phosphonomethyl)glycine product, in accordance with one preferred embodiment, the crystallization operation is preferably performed with minimal addition of heat. That is, the crystallizer 110 is preferably operated substantially adiabatically and concentration of the aqueous product slurry is achieved primarily by subsequent selective membrane separation of solubilized N-(phosphonomethyl)glycine product and water.

In accordance with one preferred embodiment, crystallizer 110 comprises a vacuum crystallizer operated without substantial heat input wherein the aqueous oxidation reaction solution is cooled as water is evaporated from the aqueous oxidation reaction solution by reducing the pressure under substantially adiabatic conditions (i.e., any heat input or removal to the crystallizer is no greater than about 200 kcal per kg of oxidation reaction solution fed to the crystallizer), and more preferably fully adiabatic conditions (although a minimal steam requirement is typically necessary in operation of a conventional vacuum system associated with the crystallizer). In an especially preferred adiabatic crystallizer system, the oxidation reaction solution is subjected to a sudden drop in pressure in a flash section that causes a fraction of the reaction solution to evaporate and form crystallizer overhead 112. This evaporation, in turn, causes the remaining reaction solution to cool resulting in the precipitation of N-(phosphonomethyl)glycine product and formation of the aqueous product slurry 111. Unlike crystallization conducted in a non-adiabatic crystallizer, the separation process in an adiabatic or substantially adiabatic crystallizer results primarily from reduction in solubility due to cooling rather than to the concentrating effect of removal of water. That is, although water is evaporated and removed in adiabatic crystallization, the amount of water removed is less as compared to heat-driven crystallization (described below).

The flash section of an adiabatic crystallization system defines an evaporation zone maintained by a vacuum system at sub-atmospheric pressure and below the vapor pressure of the aqueous oxidation reaction solution 105 fed to the crystallizer 110. The pressure maintained in the evaporation zone of the adiabatic crystallizer is generally no greater than about 55 kPa absolute, preferably from about 10 to about 28 kPa absolute, even more preferably from about 17 to about 24 kPa absolute, and still even more preferably about 20 kPa absolute. Typically, the pressure of the reaction solution immediately upstream of the evaporation zone is such that the reaction solution is subjected to a pressure reduction of at least about 135 kPa absolute, preferably from about 170 to about 650 kPa absolute more preferably from about 310 to about 515 kPa absolute, and even more preferably of about 365 kPa absolute, upon entry into the evaporation zone. The sudden decrease in pressure causes water and small molecule impurities (e.g., formaldehyde and formic acid) to flash (i.e., evaporate) from the reaction solution in the evaporation zone and form the overhead vapor stream 112 discharged from the top of the crystallizer. Normally, no greater than about 30% by weight, more preferably from about 5% to about 30% by weight, and even more preferably from about 5% to about 10% by weight of the oxidation reaction solution is discharged as vapor 112. As a result of evaporation, the remaining condensed phase portion of the oxidation reaction solution is cooled considerably, thereby resulting in precipitation of N-(phosphonomethyl)glycine product and producing aqueous product slurry 111 comprising crystalline N-(phosphonomethyl)glycine product solids suspended in mother liquor. Preferably, the cooling effect resulting from the pressure reduction is sufficient that the temperature of the aqueous product slurry is from about 20° C. to about 60° C. lower than the temperature of the oxidation reaction mixture solution introduced into the adiabatic crystallization system.

Although conducting the crystallization operation in an adiabatic or substantially adiabatic vacuum-operated crystallizer is usually preferred, the crystallization operation may alternatively comprise the addition of heat to the aqueous oxidation reaction solution in crystallizer 110 to achieve some of the water removal necessary to concentrate and crystallize the N-(phosphonomethyl)glycine product. That is, a greater proportion of the water removal requirements may be obtained in non-adiabatic crystallizer operations and shifted away from subsequent selective membrane operations. The heat used in non-adiabatic crystallizer operations is normally derived by transfer from a suitable heat transfer fluid such as steam. The operating pressure in the heat-driven evaporative crystallizer is generally maintained as noted above for adiabatic vacuum crystallization operations. During non-adiabatic crystallizer operations at least about 30% by weight, at least about 50% by weight or even more of the oxidation reaction solution may be evaporated and discharged as vapor 112. The rate of heat input to the crystallizer and the corresponding proportion of water removed by non-adiabatic crystallization (as opposed to water removal in subsequent selective membrane separation operations) is a design choice determined from many factors, including, for example, capital costs associated with the selective membrane separation unit, membrane sizing and energy costs including heating (e.g., steam) costs and the cost of supplying high pressure fluid to the selective membrane separation operations. However, in the case of non-adiabatic crystallization, it is generally preferred that less than about 50% by weight of the oxidation reaction solution is evaporated and discharged as vapor 112.

The crystallizer overhead vapor stream 112 issuing from crystallizer 110 can be condensed and at least a portion recycled to the oxidation reactor system 103 to use as a source of water for dissolving the PMIDA in aqueous feed stream or slurry 101 or introduced directly into one or more of the oxidation reaction zones. At least a portion of the crystallizer overhead is typically purged (i.e., discharged) from the system as shown by dashed line 161 in FIG. 1. Purge 161 helps to reduce the amount of impurity buildup (particularly buildup of formaldehyde, formic acid and other small molecule impurities) in the system and helps manage the water balance of the system. The purged material may, in turn, be further treated to remove impurities. For example, the purged overheads may be contacted with an oxygen-containing gas and Group VIII metal catalyst to oxidize formaldehyde and formic acid to $CO_2$ and water. The product of such oxidation treatment may be recycled to one or more of the oxidation reaction zones of the oxidation reactor system 103 and used as a source of makeup water.

The aqueous product slurry 111 collected in the bottom of the crystallizer 110 contains the bulk of the N-(phosphonomethyl)glycine product in the form of crystals along with crystallization mother liquor substantially saturated or supersaturated in N-(phosphonomethyl)glycine product and containing various impurities. Regardless of whether substantially adiabatic or non-adiabatic crystallization operations are employed, the temperature of the aqueous product slurry 111 collected in the bottom of crystallizer 110 is typically no greater than about 80° C., for example from about 40° C. to about 80° C.

As shown in FIG. 1, a first fraction 113 of the aqueous product slurry 111 comprising N-(phosphonomethyl)glycine product crystals and mother liquor is discharged from crystallizer 110 and introduced into a solids/liquid separation system 117 to produce a wet-cake product 119 and a solids-depleted stream 123. Generally, any solids/liquid separation device suitable for separating a crystal product from mother liquor may be used. However, because of the relatively high throughput and capacity requirements required by processes for the concentration and recovery of N-(phosphonomethyl) glycine products from a reaction solution resulting from the liquid phase oxidation of PMIDA substrates, preferred embodiments of the present invention typically employ liquid/solids separation devices adapted for pressure filtration, vacuum filtration, and/or centrifugation. For example, preferred liquid/solids separation devices may include vacuum drums, vacuum table filters and/or centrifuges. In a particularly preferred embodiment, product crystals are separated from the slurry fraction by centrifugation. In an especially preferred embodiment, the wet-cake product 119 is separated in a solid bowl or basket centrifuge.

For example, in one embodiment, the solids/liquid separation system 117 can suitably comprise a hydroclone (or bank of hydroclones) and a further solids/liquid separation device, preferably a centrifuge. The hydroclone forms a solids-depleted stream and a concentrated slurry enriched in precipitated N-(phosphonomethyl)glycine product that is introduced into the centrifuge to form a centrate (which is further depleted in precipitated N-(phosphonomethyl)glycine product) and the N-(phosphonomethyl)glycine product wet-cake 119. At least a portion of the solids-depleted stream 123 generated in the solids/liquid separation system (e.g., the solids-depleted stream from the hydroclone and/or the centrate) is preferably recycled back to crystallizer 110 for further recovery of the N-(phosphonomethyl)glycine product. Alternatively (or in addition), at least a portion of the solids-depleted stream 123 (e.g., the centrate) can be recycled back to one or more of the oxidation reaction zones of the reactor system 103 as shown by dashed line 123a in FIG. 1 to convert unreacted PMIDA substrate to N-(phosphonomethyl)glycine product. Furthermore, alternatively (or in addition), at least a portion of the solids-depleted stream 123 (e.g., the centrate) can be purged from the system as shown by dashed line 123b in FIG. 1. Purging a portion of the centrate helps to reduce the amount of impurity buildup (particularly larger molecule impurity buildup) in the system and thus in wet-cake 119. In a still further process alternative (or in addition), at least a portion of the solids-depleted stream 123 (e.g., the solids-depleted stream from the hydroclone and/or the centrate) can be directed to the selective membrane operation (described below) as shown by dashed line 123c in FIG. 1.

Normally, the concentration of the N-(phosphonomethyl) glycine product in the wet-cake 119 is at least about 95% (by weight of all compounds besides water), although a lower product concentration may be tolerated if the wet-cake is subsequently washed with water or blended with higher purity product. Wet-cake product 119 may be subject to further processing to generate a saleable product. Such further processing may include drying to remove excess water to generate a wet-cake or further addition of base neutralization components to generate a suitable N-(phosphonomethyl)glycine salt product or formulation of acceptable purity. For example, the N-(phosphonomethyl)glycine product in the wet-cake product 119 may be neutralized with a base or bases in a conventional manner to prepare an agronomically acceptable salt of N-(phosphonomethyl)glycine as is commonly used in glyphosate herbicidal formulations. Examples of agronomically acceptable salts of N-(phosphonomethyl)glycine contain a cation selected from alkali metal cations (e.g., potassium and sodium ions), ammonium ion, isopropyl ammonium ion, tetra-alkylammonium ion, trialkyl sulfonium ion, protonated primary amine, protonated secondary amine and protonated tertiary amine.

Haupfear et al., in U.S. Pat. No. 7,015,351 and in U.S. Application Publication No. US 2005/0059840 A1, describe various processes for concentrating and purifying an N-(phosphonomethyl)glycine product solution prepared by the oxidation of a PMIDA substrate to recover an N-(phosphonomethyl)glycine product wet-cake of acceptable purity, including both non-adiabatic heat-driven evaporative crystallizer and adiabatic vacuum-operated crystallizer operations and various recycle, purging and other process options. The entire disclosures of these publications are incorporated herein by reference.

Selective Membrane Separation Operations

A second fraction 114 of the aqueous product slurry 111 collected in crystallizer 110 is separated into a solids-enriched slurry fraction comprising N-(phosphonomethyl)glycine product crystals and a solids-depleted mother liquor fraction substantially saturated or supersaturated in N-(phosphonomethyl)glycine product. As described in greater detail below, the solids-depleted mother liquor fraction is contacted with one or more selective membranes in a membrane separation unit 130 to produce a retentate 140 enriched in N-(phosphonomethyl)glycine product relative to the solids-depleted mother liquor fraction and a permeate 132 depleted in N-(phosphonomethyl)glycine product relative to the solids-depleted mother liquor fraction.

Figure 2:
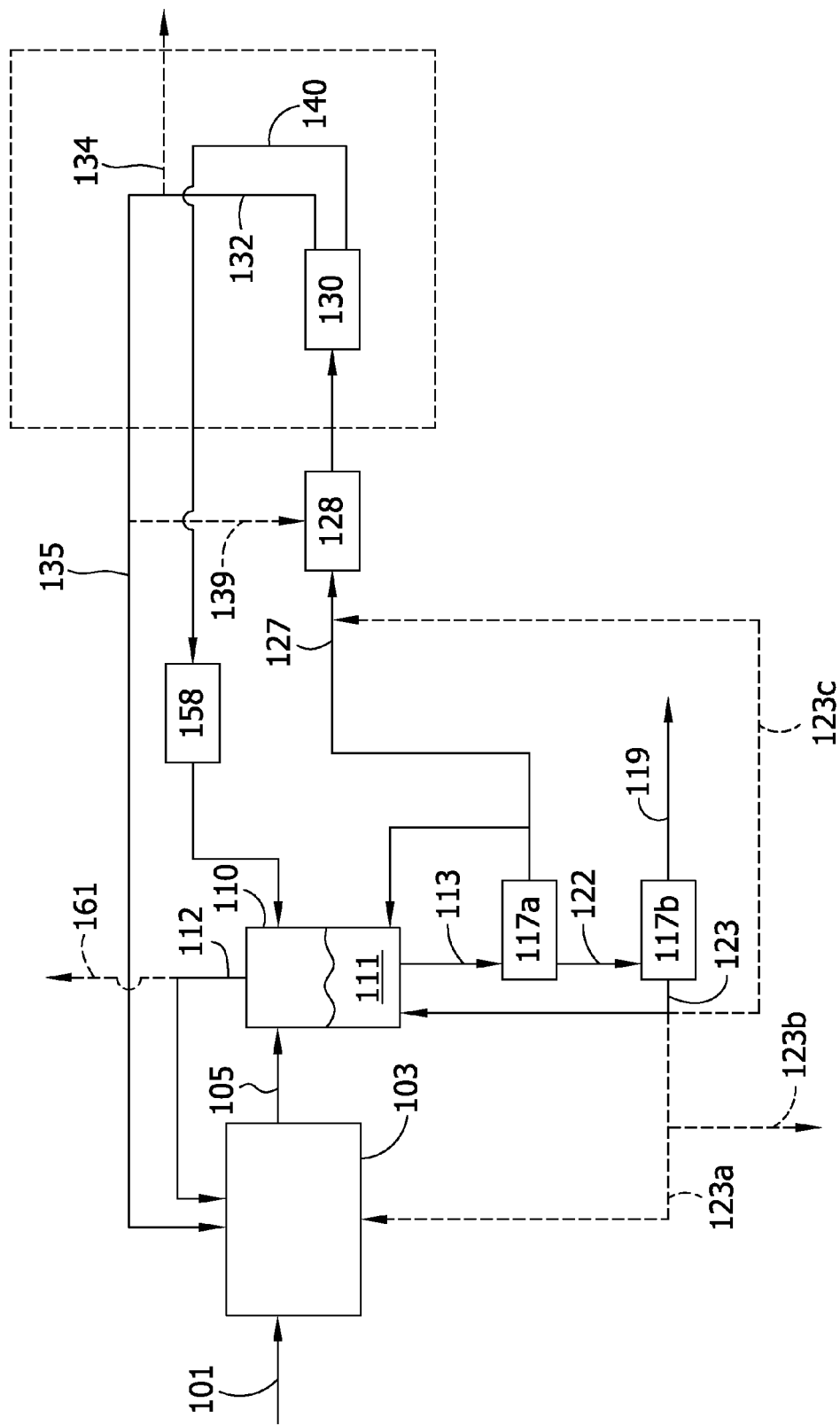
FIG. 2 is a schematic flow sheet of an alternative embodiment of the process shown in FIG. 1.

As shown in FIG. 1, in accordance with one embodiment of the present invention, second fraction 114 of the aqueous product slurry 111 from the crystallizer is transferred to a decantation vessel 125 wherein the product slurry is retained for a sufficient residence time such that a substantial fraction of the N-(phosphonomethyl)glycine product crystals settle to the bottom of the decantation vessel. A solids-enriched slurry fraction 115 underflowing from the bottom of the decantation vessel is returned to crystallizer 110, while a solids-depleted mother liquor fraction 127 is decanted at an elevation near the top of the vessel. Although a separate decantation vessel is shown in FIG. 1, it should be understood that the crystallizer can be configured and operated so as to generate a solids-depleted mother liquor fraction suitable for forwarding to the membrane separation operation. For example, all or a portion of the solids-depleted decantate issuing from the adiabatic crystallizer as described by Haupfear et al. in U.S. Pat. No. 7,015,351 can be directed to the selective membrane operation and the remainder of the decantate recycled to the oxidation reactor system 103 and/or purged from the process. Moreover, other suitable solids/liquid separation devices such as a hydroclone or bank of hydroclones may be utilized in the practice of the present invention to separate aqueous product slurry 111 collected in crystallizer 110 into a solids-enriched slurry fraction and a solids-depleted mother liquor fraction. Furthermore, as noted above, at least a portion the solids-depleted mother liquor fraction may be derived from the solids-depleted stream 123 (e.g., the solids-depleted stream from the hydroclone and/or the centrate) generated in the solids/liquid separation system 117. For example, in an alternative embodiment shown in FIG. 2, instead of subjecting a second fraction of the aqueous product slurry 111 from crystallizer 110 to decantation, a hydroclone or bank of hydroclones 117a in a solids/liquid separation system is utilized to separate aqueous product slurry 113 into a solids-depleted mother liquor fraction 127 and a concentrated slurry stream 122 enriched in precipitated N-(phosphonomethyl)glycine product. As shown in FIG. 2, at least a portion of solids-depleted mother liquor fraction 127 is preferably recycled back to crystallizer 110 for further recovery of the N-(phosphonomethyl)glycine product, while the remainder is directed to membrane separation unit 130. The concentrated slurry stream 122 issuing from hydroclone 117a is further processed in a centrifuge 117b in a solids/liquid separation system to form a further solids-depleted stream 123 (e.g., centrate) and N-(phosphonomethyl)glycine product wet-cake 119. All or a portion of the centrate can likewise be recycled back to one or more of the oxidation reaction zones of the reactor system 103, purged from the system or directed to the membrane separation unit 130 as shown by dashed lines 123a, 123b and 123c, respectively, in FIG. 2.

The aqueous solids-depleted mother liquor fraction 127 intended for selective membrane separation treatment may be collected in an optional feed tank (not shown) prior to introduction into the membrane separation unit 130. In addition to dissolved N-(phosphonomethyl)glycine product at or above the equilibrium or saturation concentration, the aqueous solids-depleted mother liquor fraction 127 typically contains an amount of suspended solids or fines in the form of retained N-(phosphonomethyl)glycine product crystals. In order to prevent fouling and the resulting loss of flux and extend the useful life of the selective membrane(s) employed in membrane separation unit 130, the suspended solids content remaining in the solids-depleted mother liquor fraction 127 is preferably controlled. Typically, solids-depleted mother liquor fraction separated from the aqueous product slurry by decantation or hydroclone operations will contain less than about 5000 ppm of suspended solids. To enhance membrane performance and extend membrane life, the suspended solids content of the solids-depleted mother liquor fraction subjected to membrane separation is preferably less than about 2000 ppm, more preferably less than about 1000 ppm, more preferably less than about 500 ppm, even more preferably less than about 100 ppm, and most preferably less than about 50 ppm. Accordingly, as shown in FIGS. 1 and 2, the solids content of solids-depleted mother liquor fraction 127 can be reduced, as necessary, to the desired level in an optional solids reduction stage 128. The suspended solids content can be readily determined by analytical methods known in the art such as by turbidity measurement (e.g., nephelometric turbidity units or NTU) and correlation of the turbidity reading to a known standard or by other methods known to those skilled in the art. As appreciated by one skilled in the art, some process streams directed to membrane separation unit 130 (e.g., the centrate of solids-depleted stream 123) may have a suitably low solids content such that further reduction of solids is unnecessary.

In accordance with one embodiment of the present invention, solids reduction stage 128 represents a point of dilution of the solids-depleted mother liquor fraction 127. The solids-depleted mother liquor fraction is diluted with a quantity of an aqueous diluent (e.g., process water) sufficient to compensate for any supersaturation in N-(phosphonomethyl)glycine product and then further diluted to dissolve suspended solids and attain the desired solids content. For example, in accordance with one preferred embodiment, a portion of the permeate 132 issuing from the membrane separation unit 130 may be recycled and used as the aqueous diluent to dilute solids-depleted mother liquor fraction 127 as shown by the dashed line 139 in FIGS. 1 and 2.

Alternatively, the solids content of the solids-depleted mother liquor fraction 127 can be reduced in solids reduction stage 128 by a filtration operation. The filtration operation can be suitably conducted in a batch mode (e.g., using bag filters) or in a continuous mode allowing for continuous flow of the solids-depleted mother liquor fraction through the solids reduction stage. Suitable continuous filters include cross-flow filters and continuous back-pulse filters wherein a portion of the filtrate is used to periodically back-pulse the filter media to dislodge and remove separated solids. Preferably, the filter media employed is capable of separating and removing suspended solids greater than about 20 μm in size, more preferably greater than about 10 μm in size, and even more preferably greater than about 5 μm in size from the solids-depleted mother liquor fraction.

In a further process alternative, the solids content can be reduced in solids reduction stage 128 by heating the solids-depleted mother liquor fraction 127 to a temperature sufficient to compensate for any supersaturation in N-(phosphonomethyl)glycine product, dissolve suspended solids and attain the desired solids content. Heating can be achieved by methods conventionally known in the art including, for example, indirect heat exchange with other process streams or a suitable heat transfer fluid such as steam. The temperature necessary to attain a substantially solids-free mother liquor fraction will depend on the composition of the solids-depleted mother liquor fraction introduced into the solids reduction stage and the extent of any supersaturation in N-(phosphonomethyl)glycine product. Typically, adequate solids reduction may be attained by increasing the temperature of the solids-depleted mother liquor fraction 127 at least about 10° C.

It should be understood that solids reduction stage 128 may comprise a combination of dilution, filtration and/or heating operations to attain a substantially solids-free mother liquor fraction 127 having the desired solids content prior to introduction into membrane separation unit 130.

The aqueous solids-depleted mother liquor fraction 127 introduced into membrane separation unit 130 will contain dissolved N-(phosphonomethyl)glycine product and typically some retained quantity of suspended N-(phosphonomethyl)glycine product crystal solids or fines and have a pH of no greater than about 2, typically from about 1.5 to about 1.8. In addition to the N-(phosphonomethyl)glycine product, the solids-depleted mother liquor fraction will typically contain various impurities including, for example, by-products and unreacted starting materials such as unreacted PMIDA substrate, N-formyl-N-(phosphonomethyl)glycine, phosphoric acid, phosphorous acid, hexamethylenetetraamine, aminomethylphosphonic acid, N-methyl-aminomethylphosphonic acid, iminodiacetic acid, formaldehyde, formic acid, and the like.

In accordance with some embodiments of the present invention, the solids-depleted mother liquor fraction 127 introduced into membrane separation unit 130 is substantially saturated or supersaturated in N-(phosphonomethyl)glycine product. That is, the concentration of dissolved N-(phosphonomethyl)glycine product in the solids-depleted mother liquor fraction initially contacted with the selective membrane is at or exceeds the equilibrium or saturation concentration at the operating temperature of the membrane separation unit. Typically, the temperature of the solids-depleted mother liquor fraction introduced into the membrane separation unit is less than about 80° C., preferably from about 40° C. to about 80° C. However, because high temperatures tend to decrease the useful life of selective membranes, the temperature of the solids-depleted mother liquor fraction introduced into the membrane separation unit is more preferably from about 40° C. to about 70° C., and even more preferably from about 40° C. to about 60° C. If necessary, solids-depleted mother liquor fraction 127 can be cooled prior to being introduced into membrane separation unit 130 by methods conventionally known in the art including, for example, indirect heat exchange with other process streams or with cooling water. Accordingly, even if the concentration of dissolved N-(phosphonomethyl)glycine product is reduced below the equilibrium concentration in solids reduction stage 128 (e.g., by dilution and/or heating), subsequent cooling prior to introduction into membrane separation unit may render the solids-depleted mother liquor fraction 127 saturated or supersaturated in N-(phosphonomethyl)glycine product. The equilibrium or saturation concentration of N-(phosphonomethyl)glycine product and the degree of saturation or supersaturation in the solids-depleted mother liquor fraction 127 introduced into membrane separation unit 130 will depend on the operating conditions employed in the crystallizer and subsequent solids/liquid separation (e.g., decanter and solids reduction) operations used to generate the solids-depleted mother liquor fraction from the aqueous product slurry.

Figure 3:
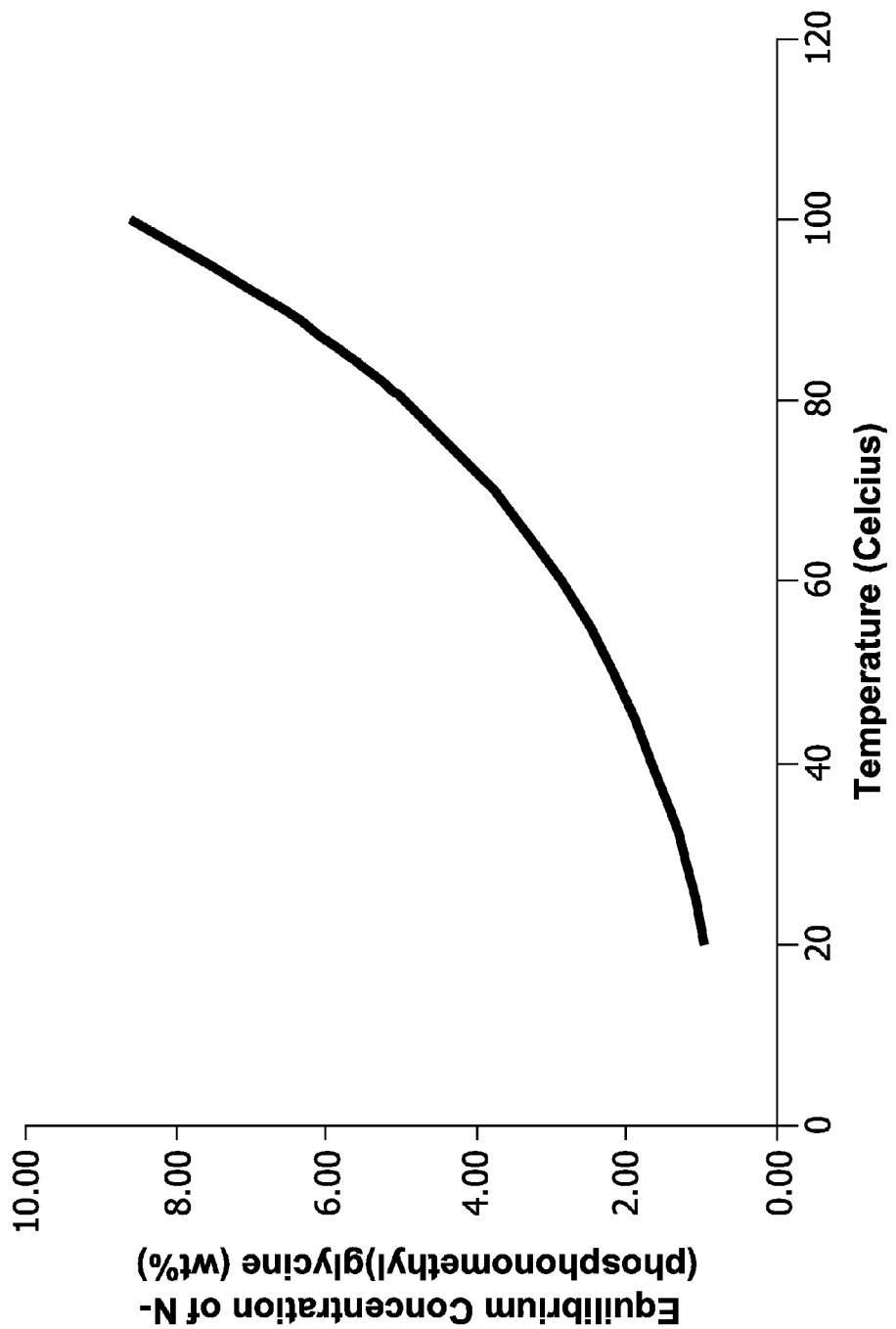
FIG. 3 is a graphical profile of the equilibrium or saturation concentration of N-(phosphonomethyl)glycine in a typical solids-depleted mother liquor solution as a function of temperature.

In accordance with the present invention, it has been discovered that membrane separation treatment of mother liquor process streams, though already saturated or supersaturated in N-(phosphonomethyl)glycine product when initially contacting the selective membrane, can nevertheless be carried out effectively while avoiding crystallization of significant quantities of N-(phosphonomethyl)glycine product in the membrane separation unit that might foul the membrane. In particular, the present invention is capable of processing mother liquor streams with an initial (i.e., at the time of initially contacting the selective membrane) relative supersaturation ($\sigma$) with respect to N-(phosphonomethyl)glycine product of at least about 0 (i.e., saturated solution), preferably at least about 0.5 or at least about 1, and up to about 2, preferably from about 0 to about 1.5, and more preferably from about 1 to about 1.5, wherein relative supersaturation is defined according to the following equation:

$$\sigma = \frac{c - c^*}{c^*}$$

wherein $c^*$ is the equilibrium or saturation concentration and $c$ is the operating concentration. FIG. 3 is a graphical profile of the equilibrium or saturation concentration of N-(phosphonomethyl)glycine in a typical aqueous solids-depleted mother liquor solution as a function of temperature. Typically, the concentration of N-(phosphonomethyl)glycine product dissolved in the saturated or supersaturated solids-depleted mother liquor fraction will be at least about 2% by weight or more.

In particular, the membrane separation unit used to treat saturated or supersaturated mother liquor streams is sized and operated in a manner that avoids significant crystallization of N-(phosphonomethyl)glycine product by providing a residence time in the selective membrane unit that is less than the induction time typically required for crystals to form. As shown in Example 3 below, crystallization induction time for solutions supersaturated in N-(phosphonomethyl)glycine product depends on the temperature and the extent of supersaturation and typically is at least about 1.5 minutes and up to about 20 minutes or longer. Preferably, the temperature of the substantially solids-free mother liquor fraction 127 introduced into the membrane separation unit 130 is maintained sufficiently high such that the induction time for N-(phosphonomethyl)glycine product crystals to form is not substantially less than the residence time through the membrane separation unit. More preferably, the residence time through the membrane separation unit is equal to or less than the induction time required for formation of N-(phosphonomethyl)glycine product crystals so as to avoid appreciable crystallization of N-(phosphonomethyl)glycine product from the mother liquor solution. For example, when subjecting a mother liquor solution having an initial relative supersaturation ($\sigma$) of about 2 to selective membrane separation at a temperature of about 50° C., the selective membrane unit is sized and operated to provide a residence time of less than about 3 minutes, preferably less than about 2 minutes, and more preferably less than about 1 minute.

The membrane separation unit 130 may be configured as either a single pass or multi-pass system and may comprise one or more nanofiltration and/or reverse osmosis membranes or modules. The membrane modules may be of various geometries and include flat (plate), tubular, capillary or spiral-wound membrane elements and the membranes may be of mono- or multilayer construction. In some embodiments, tubular membrane modules may allow for higher solids content in the mother liquor solution to be treated such that solids reduction upstream of the membrane separation unit is not required or can be significantly reduced. In order to adequately withstand the low pH conditions prevailing in the solids-depleted mother liquor fraction fed to the membrane separation unit, the separation membranes and other components (e.g., support structure) of the membrane modules are preferably constructed of suitably acid-resistant materials. For example, the separation membranes are typically constructed of organic polymers such as crosslinked aromatic polyamides in the form of one or more thin film composites. Examples of suitable nanofiltration and reverse osmosis membranes include, for example and without limitation, the S, A, D, H and K series membranes manufactured by GE Water & Process Technologies, Inc., a subsidiary of GE Infrastructure (Minnetonka, Minn.), SelRO membranes available from Koch Membrane Systems (Wilmington, Mass.), and the NF membranes available from Filmtec Corporation, a subsidiary of the Dow Chemical Company (Midland, Mich.). Specific examples of suitable nanofiltration membranes include, for example and without limitation, the DK, DL, HK, HL and KH membranes manufactured by GE Water & Process Technologies, Inc., the NF membranes (e.g., NF 40, NF 40HF, NF 50, NF 70, and NF 270) available from FilmTec Corporation, MPS-34 membrane available from Koch Membrane Systems (Wilmington, Mass.), the SU 600 membrane available from Toray (Japan), and the NTR membranes (e.g. NTR 7450 and NTR 7250) available from Nitto Electric (Japan). Specific examples of suitable reverse osmosis membranes include, for example and without limitation, the AD, AE, AG, AK, SC, SE and SG membranes available from GE Water & Process Technologies, Inc. and the SW30 reverse osmosis membrane available from FilmTec Corporation.

Nanofiltration and reverse osmosis are pressure-driven separation processes driven by the difference between the operating pressure and the osmotic pressure of the solution on the feed or retentate side of the membrane. The operating pressure in the membrane separation unit 130 will vary depending upon the type of membrane employed, as osmotic pressure is dependent upon the level of transmission of solutes through the membrane. Operating pressures in membrane separation unit 130 are suitably achieved by passing the incoming solids-depleted mother liquor fraction 127 through one or more pumps (not shown) upstream of the membrane unit, for example, a combination booster pump and high-pressure pump arrangement. Generally, nanofiltration operations exhibit lower osmotic pressures than reverse osmosis operations, given the same feed solution. For the membranes that were tested, the osmotic pressure for nanofiltration and reverse osmosis treatment of N-(phosphonomethyl)glycine product mother liquor solutions was about 1273 kPa absolute and about 2170 kPa absolute, respectively. Accordingly, the operating pressure necessary to achieve adequate water removal in permeate 132 is significantly lower in the case of nanofiltration membranes as compared to reverse osmosis membranes. The driving force for transmission of water through the membrane (i.e., permeate flux) increases with the operating pressure. However, the benefits of increased operating pressure must be weighed against the increased energy (i.e., pumping) requirements and the detrimental effects (i.e., compaction) on membrane life.

Typically, the operating pressure utilized in nanofiltration operations is less than about 4238 kPa absolute and preferably from about 2170 to about 3550 kPa absolute. As illustrated in Example 2 (Table 5) below, a permeate flux of about 565 liters per m$^2$ per day with a N-(phosphonomethyl)glycine rejection rate (i.e., measure of retention of product in retentate) of about 98% by weight can be achieved when treating a mother liquor solution containing about 3.3% by weight N-(phosphonomethyl)glycine by use of a nanofiltration membrane at an operating pressure of about 4614 kPa absolute.

Typically, the operating pressure utilized in reverse osmosis operations is at least about 690 kPa above the osmotic pressure exerted by the membrane. For many of the reverse osmosis embodiments of the present invention, operating pressures are typically greater than about 4238 kPa absolute and preferably from about 5617 to about 6996 kPa absolute, which represents an approximate driving force of 3447 kPa absolute to 4826 kPa absolute. As illustrated in Example 1 (Table 2) below, a permeate flux of about 646 liters per m$^2$ per day with a N-(phosphonomethyl)glycine rejection rate of about 99% by weight can be achieved when treating a mother liquor solution containing about 3.7% by weight N-(phosphonomethyl) glycine by use of a reverse osmosis membrane at an operating pressure of about 6996 kPa absolute. Although reverse osmosis membranes generally exhibit higher rates of N-(phosphonomethyl)glycine rejection as compared to nanofiltration membranes, this benefit may be offset by the energy requirements necessary to operate the membrane separation unit at a higher operating pressure. Selection of the appropriate membrane type in the practice of the present invention will depend on the overall economics of the process as well as the associated capital cost.

In order to maintain or enhance membrane separation efficiency and permeate flux, the membranes should be periodically cleaned so as to remove contaminants from the surface of the membrane. Suitable cleaning includes cleaning-in-place (CIP) operations wherein the surface of the membrane is exposed to a cleaning solution while installed with membrane separation unit 130. Preferred systems monitor the conductivity of permeate 132 as conductivity can be correlated to the concentration of N-(phosphonomethyl)glycine product and other components that pass through the membrane. An increase in conductivity in the permeate may indicate an increase in transmission of the N-(phosphonomethyl) glycine product through the membrane and can be used to signal the need for cleaning operations. Additionally, a fall in permeate flow with all other factors remaining constant may indicate fouling and the need for cleaning operations.

Cleaning protocols and cleaning solutions will vary depending on the type of separation membrane employed and are generally available from the membrane manufacturer. Suitable cleaning solutions may include, for example, caustic or alkaline solutions. For example, in the case of polyamide thin-film based reverse osmosis membranes, suitable cleaning solutions may include membrane cleaners available from GE Betz, Inc., a subsidiary of GE Infrastructure (Trevose, Pa.), such as (1) an alkaline, water-soluble surfactant-containing membrane cleaner that removes organic foulants and comprising diethanolamine, the trisodium salt of nitrilotriacetic acid, the trisodium salt of N-hydroxyethylenediamine triacetic acid, triethanolamine, monoethanolamine and sulfonated sodium salts of 1,1'-oxybis, tetrapropylene benzene derivatives; and/or (2) an alkaline chelating agent-containing membrane cleaner comprising trisodium phosphate (sodium phosphate, tribasic), the disodium salt of silicic acid (sodium metasilicate), sodium carbonate and sodium dodecylbenzenesulfonate. In order to not damage the membranes and unnecessarily shorten membrane life, the CIP operation is preferably conducted using a solution of a standard pH at pressure and temperature conditions known to those skilled in the art. In some applications, it may be advantageous to conduct a cleaning operation on new separation membranes prior to use in the membrane separation operation in order to improve membrane performance.

N-(phosphonomethyl)glycine product obtained in the enriched retentate 140 withdrawn from membrane separation unit 130 is preferably crystallized and ultimately recovered as part of wet-cake product 119 by recycling the retentate back to crystallizer 110 but, optionally, separate crystallization equipment can also be utilized. Due to process conditions and/or heat losses from the membrane separation unit, the temperature of retentate 140 may be sufficiently low such that there is a risk that N-(phosphonomethyl)glycine product may crystallize from the retentate prior to being returned to the crystallizer. Accordingly, it may be necessary to provide heat transfer equipment 158 for heating and maintaining the temperature of the recycled retentate at a temperature sufficiently high to avoid premature crystallization.

In one embodiment of the present invention, a first fraction 135 of permeate 132 withdrawn from membrane separation unit 130 is recycled to oxidation reactor system 103. A second fraction 134 can optionally be purged from the system. In accordance with one embodiment of the present invention, substantially all of the permeate withdrawn from the membrane separation unit is recycled to the oxidation reactor system. Under typical processing conditions, in addition to water, permeate 132 may contain up to 2.5% by weight of impurities, including, for example, phosphoric acid, phosphorous acid, aminomethylphosphonic acid, formaldehyde, formic acid, chlorides and the like.

The amount of water required to be evaporated in crystallizer 110 to sufficiently concentrate the oxidation reaction solution is reduced by about the amount of water in the substantially solids-free mother liquor fraction 127 passed through the selective membrane unit 130 to permeate 132. Under typical process conditions in a single pass membrane separation unit, a permeate 132 to mother liquor 127 feed ratio of from about 0.3 to about 0.6 can be achieved with an N-(phosphonomethyl)glycine rejection rate of about 98% or higher. As appreciated by one skilled in this art, permeate to feed ratios and N-(phosphonomethyl)glycine rejection rates are selected with consideration of a variety of system factors including, for example, equipment cost and sizing, oxidation reaction solution concentrations and N-(phosphonomethyl) glycine product concentrations.

Figure 4:
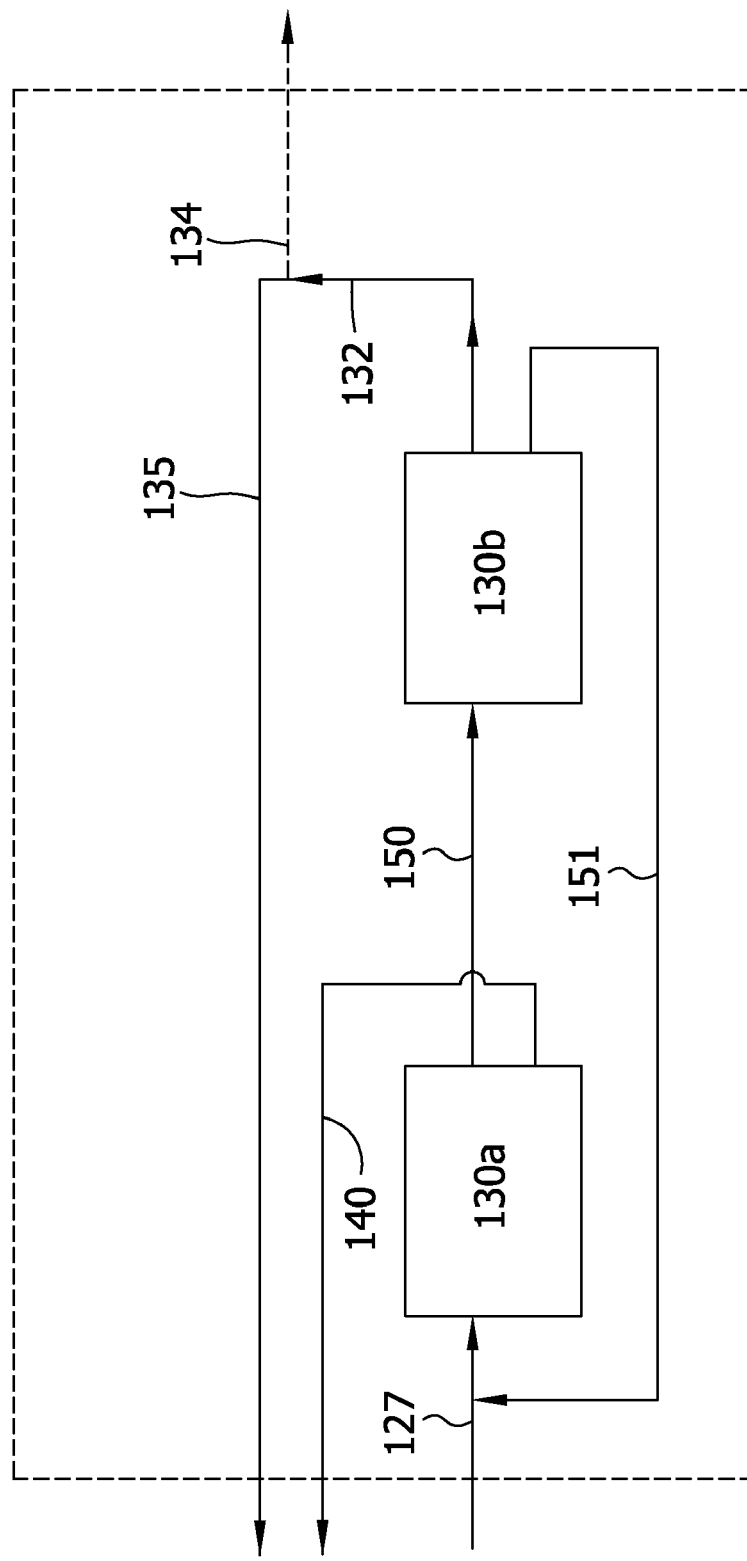
FIG. 4 is a schematic flow sheet of a two-pass selective membrane system for use in the process shown in FIGS. 1 and 2.

In accordance with one embodiment of the present invention, and as illustrated in FIG. 4, a two-pass membrane separation unit 130a and 130b is used in the process shown in FIGS. 1 and 2 to concentrate N-(phosphonomethyl)glycine product in the solids-depleted mother liquor fraction 127. The substantially solids-free mother liquor fraction 127 is contacted with a nanofiltration membrane in separation unit 130a to produce a first retentate 140 enriched in N-(phosphonomethyl)glycine product and a first permeate 150 depleted in N-(phosphonomethyl)glycine product. First permeate 150 is contacted with a reverse osmosis membrane in separation unit 130b to produce a second retentate 151 enriched in N-(phosphonomethyl)glycine product and a second permeate 132 depleted in N-(phosphonomethyl)glycine product. A first fraction 135 of second permeate 132 can be recycled to oxidation reactor system 103 and, optionally, a second fraction 134 can be purged from the system. The second retentate 151 is recycled to the nanofiltration membrane separation unit 130a.

The use of a multi-pass system comprising a first nanofiltration membrane unit 130a and a second reverse osmosis membrane unit 130b minimizes N-(phosphonomethyl)glycine product loss. The transmission rate of N-(phosphonomethyl)glycine product through the more porous nanofiltration membrane is greater than the transmission rate through a reverse osmosis membrane separation unit. However, the second reverse osmosis membrane separation unit 130b allows N-(phosphonomethyl)glycine product to be recovered from the first permeate 150 transmitted by the nanofiltration membrane 130a. Such a multi-pass system allows the permeate flux to remain high even as osmotic pressure increases. The two-pass system illustrated in FIG. 4 allows for an overall permeate to mother liquor feed ratio of from about 0.3 to 0.6 with an overall N-(phosphonomethyl)glycine rejection rate of at least about 99% by weight in treating a mother liquor solution containing about 2.5% by weight N-(phosphonomethyl)glycine product.

Figure 5:
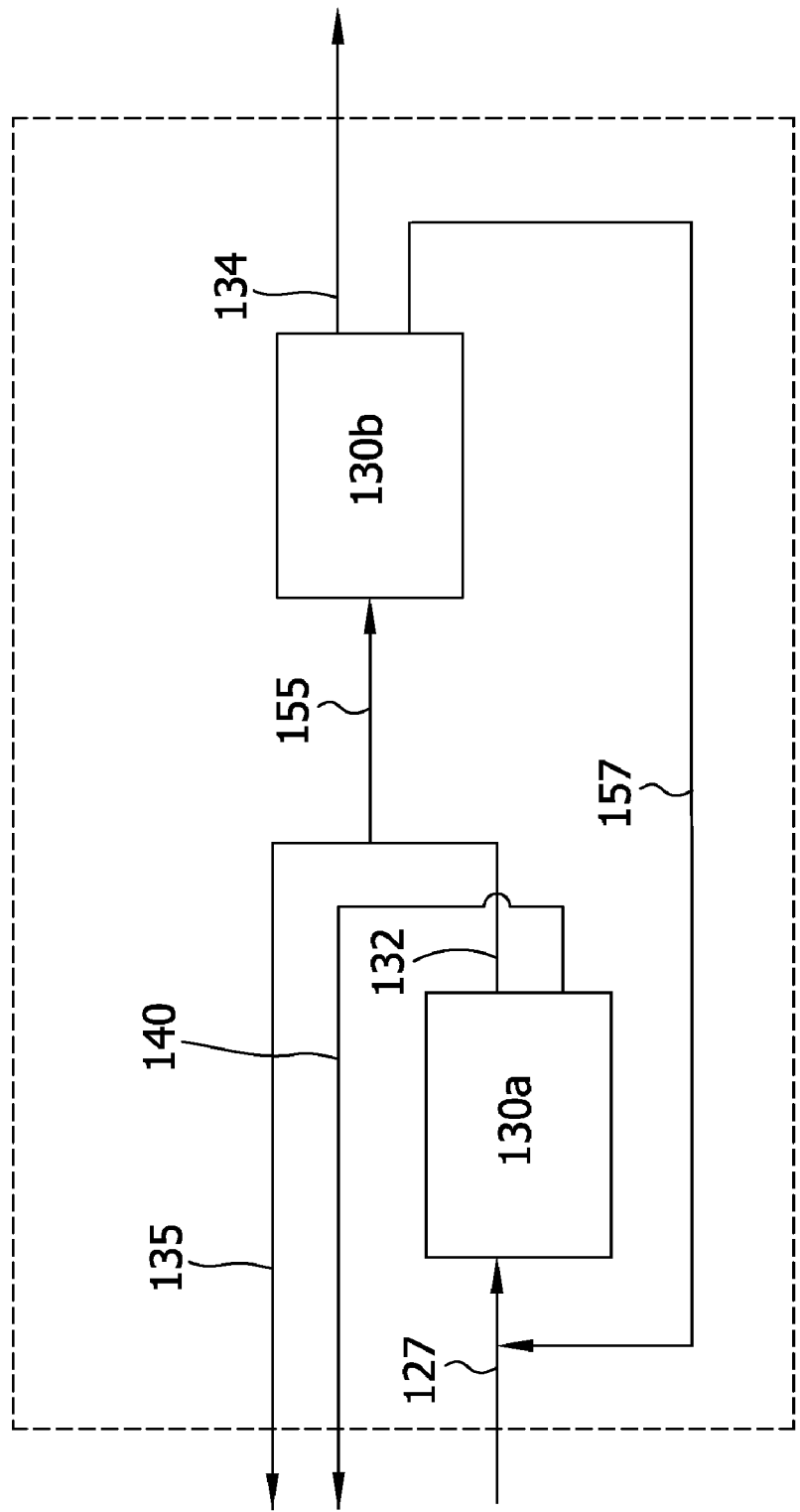
FIG. 5 is a schematic flow sheet of a second two-pass selective membrane system for use in the process shown in FIGS. 1 and 2.

As illustrated in FIG. 5, a second membrane separation unit can be used to recover N-(phosphonomethyl)glycine product from a portion of the permeate stream generated in the membrane separation unit of a process as depicted in FIGS. 1 and 2 prior to purging from the system. The substantially solids-free mother liquor fraction 127 is contacted with a nanofiltration membrane in membrane separation unit 130a to produce first retentate 140 enriched in N-(phosphonomethyl) glycine product and first permeate 132 depleted in N-(phosphonomethyl)glycine product. First fraction 135 of first permeate 132 can be recycled to oxidation reactor system 103, while a second fraction 155 is introduced into a second membrane separation unit 130b and contacted with a reverse osmosis membrane to produce a second retentate 157 enriched in N-(phosphonomethyl)glycine product and second permeate 134 depleted in N-(phosphonomethyl)glycine product. Second permeate 134 is purged and second retentate 157 is recycled to the nanofiltration membrane separation unit 130a. The two-pass system illustrated in FIG. 5 allows for an overall permeate to mother liquor feed ratio of from about 0.3 to 0.6 with an overall N-(phosphonomethyl)glycine rejection rate of at least about 99% by weight in treating a mother liquor solution containing about 2.5% by weight N-(phosphonomethyl)glycine product.

EXAMPLES

The following examples are simply intended to further illustrate and explain the present invention. The invention, therefore, should not be limited to any of the details in these examples.

Experiments were undertaken to determine if membrane technology could be successfully applied to solids-depleted mother liquor streams that were saturated or supersaturated with N-(phosphonomethyl)glycine. The mother liquor used in these experiments comprised a solids-depleted mother liquor originally collected from a centrifugation step used to generate N-(phosphonomethyl)glycine wet-cake from a crystallization product slurry at a glyphosate manufacturing facility, and therefore had a pH and composition similar to the crystallizer mother liquor typically generated in such a process. The pH of the mother liquor was very acidic, with a pH ranging from about 1.5 and about 1.8. The mother liquor comprised N-(phosphonomethyl)glycine and impurities commonly produced during the liquid phase oxidation of a PMIDA substrate as noted above.

High performance liquid chromatography (HPLC) was used to measure the levels of N-(phosphonomethyl)glycine and select impurities in mother liquor feed, retentate, and permeate samples. Analysis was performed using Varian instruments (pumps, lamps, etc.) that employed ionic chromatographic columns. The levels of some impurities such as chloride ions were measured using basic titration techniques known to those skilled in the art.

Laboratory Evaluation System

Figure 6:
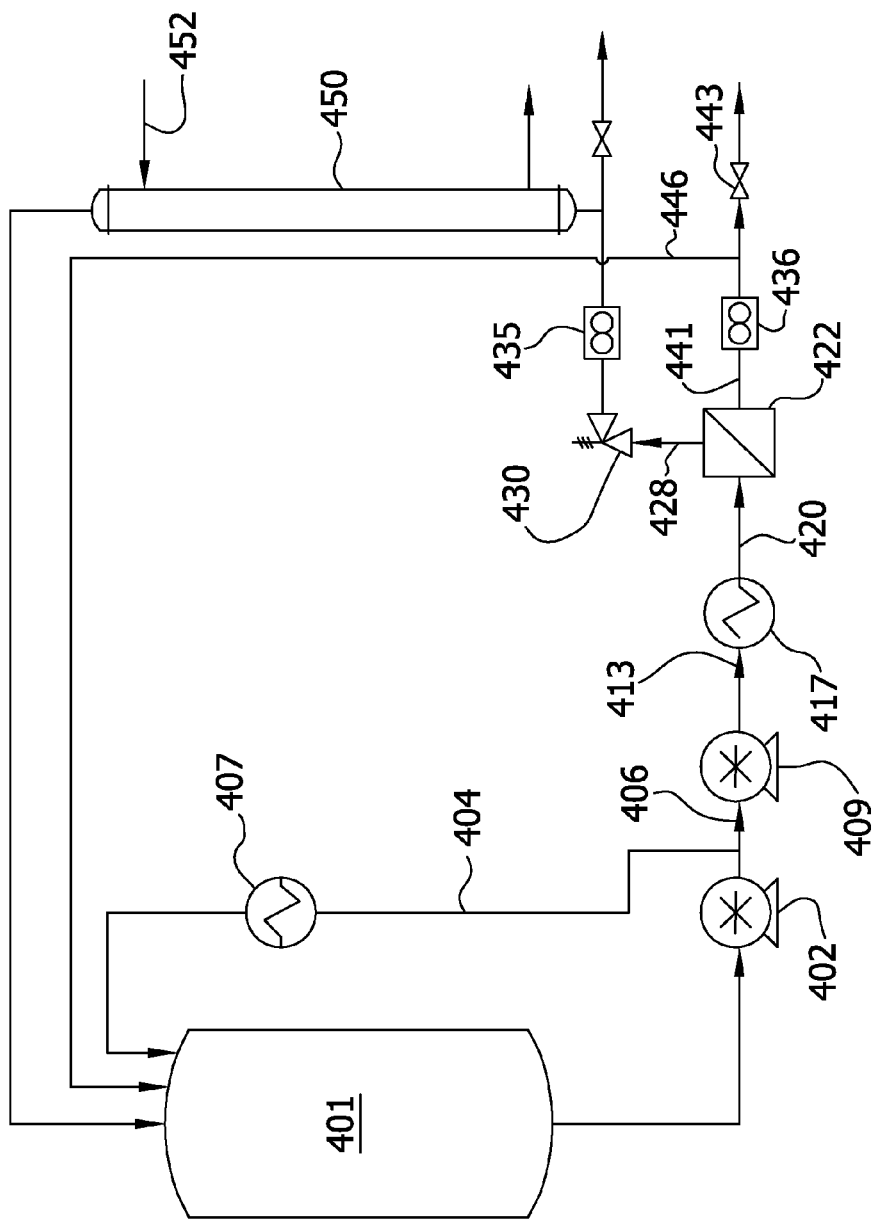
FIG. 6 is a schematic flow sheet of the apparatus used in the lab-scale experiments described below in the Examples.

Laboratory experiments were conducted using a setup shown schematically in FIG. 6 that allowed for the processing of solids-depleted mother liquors that were saturated or supersaturated in N-(phosphonomethyl)glycine. The laboratory evaluation system included a mother liquor feed vessel 401, three heat exchangers 407, 417 and 450, two pumps 402 and 409, a membrane separation unit 422 containing a spiral-wound membrane, and various process control equipment including valves, pressure indicators, and temperature controllers.

The first pump 402 was a small centrifugal pump that was used as a booster pump. Booster pump 402 served two purposes. Primarily, the booster pump provided a pressurized mother liquor feed stream 406 for high pressure pump 409. The booster pump also recycled a portion 404 of the mother liquor feed it removed from feed vessel 401 through heat exchanger 407 back to the feed vessel. This provided mixing of the contents of feed vessel 401 and a source of heat input via indirect heat exchange. Feed vessel 401 was also equipped with an internal steam heating coil (not shown) that was used to keep the contents of the feed vessel at a given setpoint temperature.

Pressurized mother liquor feed stream 406 from booster pump 402 was pressurized further by high pressure positive displacement pump 409 (Wanner diaphragm pump) that was capable of generating approximately 15.1 liters/min at 6996 kPa. A variable speed drive was installed on the pump drive to allow for feed flow rate control. High pressure pump 409 was used to send a highly pressurized mother liquor feed stream 413 through heat exchanger 417 and on to membrane separation unit 422. Heat exchanger 417 used cooling water to lower the temperature of mother liquor feed stream 413 to the target operating temperature of membrane separation unit 422. This setup allowed for the generation of a supersaturated mother liquor feed stream 420 that would then be processed by membrane separation unit 422.

Spiral-wound membranes of various sizes were tested in the laboratory evaluation system. Membranes were tested in bench configurations of 1.8 inches (0.046 m) or 2.5 inches (0.64 m) in diameter and 12 inches (0.0305 m) or 40 inches (1.016 m) in length. A pressure transducer and thermocouple (both not shown) were installed just prior to membrane separation unit 422 to allow for monitoring and continuous logging of the mother liquor feed pressure and feed temperature, respectively. The operating pressure was controlled by a throttle valve 430 positioned on the outlet from which retentate 428 was withdrawn from membrane separation unit 422. Operating pressures varied from about 1135 to about 6996 kPa absolute, while operating temperatures varied from about 25° C. to about 65° C.

In all laboratory experiments, retentate 428 was recycled to feed vessel 401 after it exited membrane separation unit 422. The retentate passed through a flow meter 435 that provided for monitoring and continuous data logging of the retentate flow rate. The retentate also passed through indirect heat exchanger 450 supplied with steam 452 in route to feed vessel 401, in order to heat the retentate to the temperature of the contents of the feed vessel in order to minimize the risk of crystallization when cooler, supersaturated retentate was mixed in the feed vessel. The permeate 441 exiting the housing of membrane separation unit 422 was also passed through a flow meter 436 that provided for monitoring and continuous data logging of the permeate flow rate.

The permeate 441 could be diverted to a waste stream 443 or recycled to feed vessel 401 in permeate recycle stream 446 depending upon the type of experiment conducted. During a "recycle" experiment, permeate was recycled to feed vessel 401 along with the retentate to provide a constant mother liquor feed composition throughout the experiment. This type of experiment was used to generate data regarding the stability of membrane flux and rejection characteristics. During a "batch concentration" experiment, the permeate would be diverted to waste, while the retentate was recycled to feed vessel 401. This type of experiment allowed for the evaluation of membrane flux and rejection characteristics while the concentration of N-(phosphonomethyl)glycine in the mother liquor feed was increasing.

Pilot-Scale Evaluation System

Figure 7:
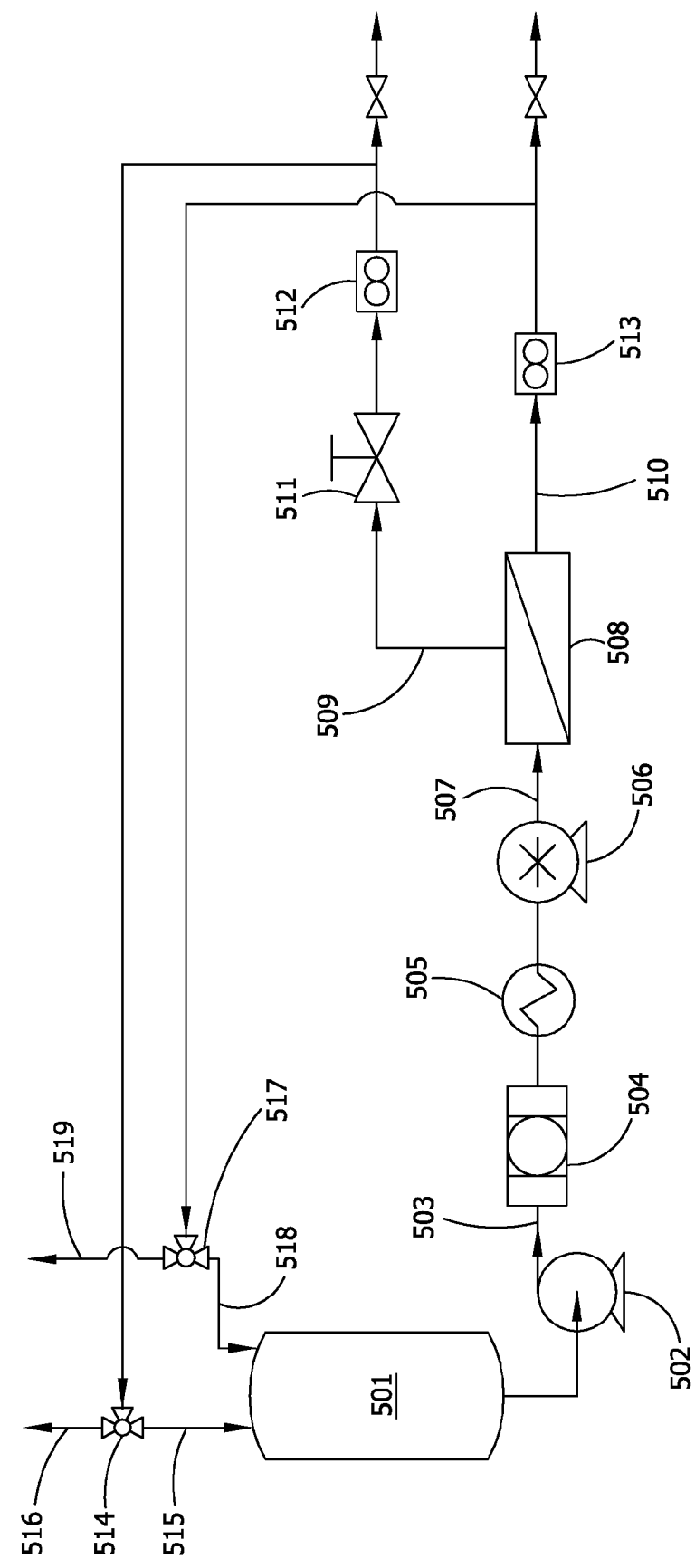
FIG. 7 is a schematic flow sheet of the apparatus used in the pilot-scale experiments described below in the Examples.

Pilot-scale experiments were conducted using a setup shown schematically in FIG. 7 that allowed for the processing of solids-depleted mother liquors that were saturated or supersaturated in N-(phosphonomethyl)glycine. The pilot-scale evaluation system included a mother liquor feed vessel 501, a heat exchanger 505, two pumps 502 and 506, a membrane separation unit 508 containing eight spiral-wound membranes in series, and various process control equipment including valves, pressure indicators, and temperature controllers.

Feed vessel 501 was equipped with a steam jacket (not shown) that was used to maintain the contents of the feed vessel at a given setpoint temperature. The first pump 502 was a small centrifugal pump that was used as a booster pump. Booster pump 502 provided a pressurized mother liquor feed stream 503 for high pressure pump 506. The pressurized feed stream 503 was passed through a set of 5 micron cartridge filters 504 that protected high pressure positive displacement pump 506 from particulates. Pressurized feed stream 503 was then passed through heat exchanger 505 so that it could be cooled to a targeted operating temperature of the membranes separation unit 508.

Pressurized mother liquor feed stream 503 from booster pump 502 was pressurized further by high pressure positive displacement pump 506 (Wanner diaphragm pump) that was capable of generating approximately 60.6 liters/min at 6996 kPa. A variable speed drive was installed on the pump drive to allow for feed flow rate control. High pressure pump 506 was used to send a highly pressurized mother liquor feed stream 507 to the membrane separation unit 508.

The membrane separation unit 508 of the pilot-scale evaluation system contained eight spiral-wound reverse osmosis membranes or nanofiltration membranes in series such that the retentate from a membrane was the feed for the next membrane in series and permeates from each membrane were combined to form one composite permeate stream 510. The spiral-wound membranes were of a 4040 configuration, having a diameter of 4 inches (0.102 m) and a length of 40 inches (1.016 m). A pressure transducer and thermocouple (both not shown) were installed just prior to membranes separation unit 508 to allow for monitoring and continuous logging of the mother liquor feed pressure and feed temperature, respectively. A separate pressure transducer (not shown) was also installed on the retentate outlet to allow for the calculation of the pressure drop across membranes separation unit 508. The operating pressure was controlled by a throttle valve 511 positioned on the outlet from which retentate 509 was withdrawn from membrane separation unit 508. Operating pressures varied from about 1135 to about 6996 kPa absolute when testing reverse osmosis membranes and from about 2534 to about 3149 kPa absolute when testing nanofiltration membranes, while operating temperatures varied from about 25° C. to about 65° C.

Two types of tests were conducted in pilot-scale experiments. In "static" testing three-way retentate return valve 514 was positioned such that retentate 509 was directed to a retentate recycle stream 515 and returned to mother liquor feed vessel 501. The retentate 509 passed through a flow meter 512 that provided for monitoring and continuous data logging of the retentate flow rate. A three-way permeate return valve 517 was positioned such that permeate 510 exiting membrane separation unit 508 was directed to a permeate recycle stream 518 and returned to the mother liquor feed vessel 501. The permeate 510 passed through a flow meter 513 that provided for monitoring and continuous data logging of the retentate flow rate.

During "dynamic" testing, a fresh solids-depleted mother liquor solution (i.e., centrate collected at the glyphosate manufacturing facility) was continuously fed (not shown) to feed vessel 501. The three-way retentate return valve 514 was positioned such that retentate 509 was diverted to a retentate recirculation stream 516 and returned to the glyphosate manufacturing process that generated the solids-depleted mother liquor solution. The three-way permeate return valve 517 was positioned such that permeate 510 was diverted to a permeate recirculation stream 519 and likewise returned to the glyphosate manufacturing process.

Example 1

Concentration of N-(phosphonomethyl)glycine Mother Liquor by Contacting a Supersaturated N-(phosphonomethyl)glycine Mother Liquor Stream with a Reverse Osmosis Membrane The performance of reverse osmosis membranes was evaluated for the processing of solids-depleted mother liquor streams under varying degrees of N-(phosphonomethyl)glycine supersaturation. Four series of data were generated in Example 1: data generated under a laboratory "recycle" experiment; data generated under a laboratory "batch concentration" experiment; data generated under a laboratory Design of Experiments test; and data generated under pilot-scale "dynamic" testing.

In the laboratory "recycle" experiment, supersaturation was generated by dissolving increasing amounts of N-(phosphonomethyl)glycine wet-cake in a solids-depleted mother liquor, and then cooling the solution to the target operating temperature prior to introduction to the membrane separation unit. The reverse osmosis membrane used in the experiment was a spiral-wound, polyamide thin-film based membrane with a nominal Molecular Weight Cut-Off (MWCO) of 100 daltons (GE Water & Process Technologies, Inc.). The evaluation was conducted such that the mother liquor feed temperature to the membrane separation unit was controlled at 50° C. and the feed pressure was maintained at 4238 kPa absolute. Several samples of mother liquor feed, retentate, and permeate were collected for each run and were averaged to produce the data shown in Table 1. Table 1 provides the mother liquor feed concentrations of N-(phosphonomethyl)glycine, the relative supersaturation at each test condition, percent N-(phosphonomethyl)glycine rejection (i.e., recovery in retentate) and the permeate flux for each run.

TABLE 1

Concentration of Supersaturated N-(phosphonomethyl)glycine Mother Liquor by Contact with a Reverse Osmosis Membrane with Permeate Recycle in Laboratory Evaluation System

| Average feed concentration of N-(phosphonomethyl)glycine (% by weight) | Average relative supersaturation ($\sigma$) at 50° C. | Observed Permeate Flux (Liters per $m^2$ per day) | Observed Rejection of N-(phosphonomethyl) glycine (%) |
|---|---|---|---|
| 2.95 | 0.21 | 449 | 97.7 |
| 3.65 | 0.50 | 406 | 97.4 |
| 4.25 | 0.74 | 402 | 96.8 |
| 5.15 | 1.13 | 363 | 96.5 |

As can be seen from Table 1, the spiral-wound reverse osmosis membrane was successfully used to process a solids-depleted mother liquor stream supersaturated in N-(phosphonomethyl)glycine. Testing indicated that rejection rates of greater than 96% and permeate fluxes higher than 350 liters per $m^2$ per day could be achieved when operating the membrane at 50° C. and 4238 kPa absolute.

In a laboratory "batch concentration" experiment, supersaturation was generated by the continuous removal of permeate from the laboratory evaluation system which resulted in an increase in the concentration of N-(phosphonomethyl)glycine and impurities in the mother liquor feed. The reverse osmosis membrane used in this experiment was a spiral-wound, polyamide thin-film based membrane with a nominal MWCO of 100 daltons (GE Water & Process Technologies, Inc.). The experiment was conducted such that the mother liquor feed temperature to the membrane separation unit was controlled at 50° C. and the operating pressure was maintained at 6996 kPa absolute. Several samples of mother liquor feed, retentate, and permeate were collected throughout the experiment as permeate was removed from the system. The results are reported in Table 2 below.

N-(phosphonomethyl)glycine supersaturation, while at the same time exhibiting high flux rates and high rejection rates. The average flux rate observed in Table 2 was 552 liters per $m^2$ per day, while the average rejection of N-(phosphonomethyl)glycine observed was 98.9%. No plugging of process lines or fouling on the membrane surface due to spontaneous nucleation and crystallization of N-(phosphonomethyl)glycine was observed.

The performance of a spiral-wound SW30-type reverse osmosis membrane (FilmTec Corporation) was evaluated in a Design of Experiments test wherein the mother liquor feed composition and feed pressure were altered accordingly. The reverse osmosis membrane used had a 2540 configuration (i.e., a diameter of 2.5 inches (0.064 m) and a length of 40 inches (1.016 m)). The mother liquor feed pressure to the membrane separation unit varied from about 4234 to about 6308 kPa, and the concentration of N-(phosphonomethyl)glycine in the mother liquor feed varied from about 3.2 to about 5.2% by weight. The experiment was conducted such that the mother liquor feed temperature to the membrane separation unit was controlled at 50° C. Six conditions were

TABLE 2

Concentration of Supersaturated N-(phosphonomethyl)glycine Mother Liquor by Contact with a Reverse Osmosis Membrane without Permeate Recycle in Laboratory Evaluation System

| Feed concentration of N-(phosphonomethyl) glycine (% by weight) | Relative Supersaturation (σ) at 50° C. | Permeate to Feed ratio | Permeate Flux (Liters per $m^2$ per day) | Rejection of N-(phosphonomethyl) glycine (%) |
|---|---|---|---|---|
| 2.93 | 0.09 | 0.05 | 857 | 99.2 |
| 2.93 | 0.10 | 0.10 | 904 | 99.1 |
| 3.14 | 0.16 | 0.15 | 847 | 99.3 |
| 3.29 | 0.23 | 0.20 | 741 | 99.4 |
| 3.52 | 0.29 | 0.25 | 702 | 99.3 |
| 3.76 | 0.37 | 0.30 | 646 | 99.3 |
| 4.10 | 0.49 | 0.35 | 548 | 99.3 |
| 4.51 | 0.60 | 0.40 | 461 | 99.3 |
| 4.92 | 0.72 | 0.45 | 405 | 99.1 |
| 5.37 | 0.88 | 0.50 | 282 | 99.0 |
| 6.18 | 1.11 | 0.55 | 182 | 98.5 |
| 7.18 | 1.39 | 0.60 | 51 | 96.0 |

As can be seen from Table 2, the spiral-wound reverse osmosis membrane can be successfully employed to process solids-depleted mother liquor streams having high levels of evaluated and samples were collected at each condition once the process had stabilized for thirty minutes. The results are reported in Table 3 below.

TABLE 3

Design of Experiment Testing for Concentration of Supersaturated N-(phosphonomethyl)glycine Mother Liquor by Contact with an SW30 Reverse Osmosis Membrane in Laboratory Evaluation System

| Feed Pressure (kPa) | Feed Concentration of N-(phosphonomethyl) glycine (% by weight) | Relative Supersaturation (σ) of feed at 50° C. | Permeate Flux (Liters per $m^2$ per day) | Rejection of N-(phosphonomethyl) glycine (%) |
|---|---|---|---|---|
| 4285 | 3.3 | 0.48 | 462 | 99.9 |
| 5289 | 3.3 | 0.48 | 692 | 99.5 |
| 6284 | 3.2 | 0.47 | 878 | 99.8 |
| 4316 | 5.2 | 1.27 | 326 | 99.6 |
| 5305 | 5.1 | 1.22 | 522 | 99.8 |
| 6308 | 5.1 | 1.24 | 684 | 99.9 |

As can be seen from Table 3, an SW30 spiral-wound reverse osmosis membrane can be successfully employed to process solids-depleted mother liquor streams having high levels of N-(phosphonomethyl)glycine supersaturation, while at the same time exhibiting high flux rates and high rejection rates. Rejection rates of greater than 99% were observed for each condition of the Design of Experiments test. No plugging of process lines or fouling on the membrane surface due to spontaneous nucleation and crystallization of N-(phosphonomethyl)glycine was observed.

"Dynamic" testing in the pilot-scale evaluation system was conducted using spiral-wound, polyamide thin-film based reverse osmosis membranes with a nominal MWCO of 100 daltons (GE Water & Process Technologies, Inc.) at an average operating temperature of 50° C. while the operating pressure varied from about 5556 to about 6499 kPa. The membranes in the pilot unit were used approximately 3000 hours to process solids-depleted mother liquor solutions prior to the start of "dynamic" testing. Before the test, the reverse osmosis membranes were cleaned using alkaline cleaning solutions, first containing a water-soluble surfactant-containing membrane cleaner, followed by a solution containing an alkaline chelating agent-containing membrane cleaner of the types described above and available from GE Betz, Inc. (Trevose, Pa.). Mother liquor feed, retentate, and permeate samples were collected from the system as the system was operated. Results are reported below in Table 4.

process lines or fouling on the membrane surface due to spontaneous nucleation and crystallization of N-(phosphonomethyl)glycine was observed.

The data presented from Table 4 is representative of the data generated during static testing of spiral-wound, polyamide thin-film based reverse osmosis membranes with a nominal MWCO of 100 daltons in the pilot unit.

Example 2

Design of Experiment Testing for Concentration of Supersaturated N-(phosphonomethyl)glycine Mother Liquor by Contact with a Nanofiltration Membrane This example illustrates experiments conducted utilizing spiral-wound nanofiltration membranes. Design of Experiment (DOE) testing was performed using the laboratory evaluation system. Pilot-scale testing was conducted using the pilot-scale evaluation system operated in a "static" mode.

The performance of a spiral-wound, polyamide thin-film based nanofiltration membrane with a MWCO of 250 daltons (GE Water & Process Technologies, Inc.) was evaluated through a Design of Experiments test wherein the mother

TABLE 4

Concentration of Supersaturated N-(phosphonomethyl) glycine Mother Liquor by Contact with Reverse Osmosis Membranes during Dynamic Testing in Pilot-Scale Evaluation System

| Feed concentration of N-(phosphonomethyl) glycine (% by weight) | Relative Supersaturation ($\sigma$) of feed at 50° C. | Relative Supersaturation ($\sigma$) generated in retentate at 50° C. | Permeate to Feed ratio | Permeate Flux (Liters per m² per day) | Rejection of N-(phosphonomethyl) glycine (%) |
|---|---|---|---|---|---|
| 2.10 | −0.10 | 0.44 | 0.44 | 384 | 98.9 |
| 1.85 | −0.20 | 0.28 | 0.42 | 372 | 99.2 |
| 1.77 | −0.22 | 0.28 | 0.44 | 383 | 99.2 |
| 1.89 | −0.18 | 0.25 | 0.43 | 374 | 99.2 |
| 1.85 | −0.22 | 0.30 | 0.44 | 389 | 99.3 |
| 2.12 | −0.09 | 0.29 | 0.42 | 364 | 99.3 |
| 1.69 | −0.26 | 0.09 | 0.43 | 377 | 99.4 |
| 3.43 | 0.45 | 1.00 | 0.26 | 231 | 99.1 |
| 3.12 | 0.31 | 0.73 | 0.27 | 237 | 99.2 |
| 2.94 | 0.22 | 0.59 | 0.31 | 267 | 99.3 |
| 3.04 | 0.28 | 0.65 | 0.29 | 280 | 99.2 |
| 3.58 | 0.49 | 1.11 | 0.26 | 236 | 99.2 |
| 3.89 | 0.60 | 1.05 | 0.28 | 255 | 99.2 |
| 3.52 | 0.46 | 0.93 | 0.29 | 272 | 99.3 |

As can be seen from Table 4, the set of spiral-wound reverse osmosis membranes can be successfully employed to process solids-depleted mother liquor having varying degrees of N-(phosphonomethyl)glycine supersaturation. When the mother liquor feed was not supersaturated with N-(phosphonomethyl)glycine, the average rejection of N-(phosphonomethyl)glycine observed was 99.2%, while the average flux rate observed was 378 liters per m² per day. When the mother liquor feed was supersaturated with N-(phosphonomethyl)glycine, the average rejection of N-(phosphonomethyl)glycine observed was 99.2%, while the average flux rate observed was only 254 liters per m² per day. No plugging of liquor feed composition, feed pressure, and feed flow rate were altered accordingly. The nanofiltration membrane used had a 2540 configuration. The mother liquor feed flow rate varied from about 9.5 to about 13.2 liters per minute, the feed pressure varied from about 3548 to about 5617 kPa, and the concentration of N-(phosphonomethyl)glycine in the mother liquor feed varied from about 2.3 to about 4.0% by weight. The mother liquor feed temperature to the membrane separation unit was maintained at 50° C. throughout the experiment. Eleven conditions were evaluated and samples were collected at each condition once the process had stabilized for thirty minutes. The results are reported in Table 5 below.

TABLE 5

Design of Experiment Testing for Concentration of
Supersaturated N-(phosphonomethyl)glycine Mother Liquor by
Contact with a Nanofiltration Membrane in Laboratory
Evaluation System

| Feed Flow Rate (L/min) | Feed Pressure (kPa) | Feed Concentration of N-(phosphonomethyl) glycine (% by weight) | Relative Supersaturation ($\sigma$) of feed at 50° C. | Permeate Flux (Liters per m$^2$ per day) | Rejection of N-(phosphonomethyl) glycine (%) |
|---|---|---|---|---|---|
| 9.6 | 5595 | 2.29 | 0.01 | 1042 | 98.2% |
| 13.5 | 5600 | 2.31 | 0.00 | 1168 | 98.7% |
| 13.3 | 3576 | 2.32 | 0.02 | 660 | 98.4% |
| 9.8 | 3566 | 2.29 | −0.01 | 633 | 98.1% |
| 11.4 | 4626 | 3.35 | 0.44 | 565 | 98.3% |
| 11.4 | 4617 | 3.31 | 0.42 | 590 | 98.3% |
| 11.4 | 4614 | 3.33 | 0.44 | 564 | 98.3% |
| 9.5 | 3564 | 4.05 | 0.69 | 259 | 97.2% |
| 9.3 | 5612 | 4.07 | 0.73 | 547 | 98.2% |
| 13.4 | 3544 | 4.08 | 0.67 | 430 | 97.4% |
| 13.7 | 5626 | 4.10 | 0.71 | 690 | 98.5% |

As can be seen from Table 5, a nanofiltration membrane could also be used to treat a solids-depleted mother liquor that was saturated or supersaturated with N-(phosphonomethyl) glycine. Also, the nanofiltration membrane exhibited rejection rates that were only slightly less than the rejection rates of the reverse osmosis membrane.

The performance of a spiral-wound MPS-34 nanofiltration membrane (Koch Membrane Systems) was evaluated through a Design of Experiments test similar to that conducted on the nanofiltration membrane from GE Water & Process Technologies, Inc. as described above. The nanofiltration membrane had a 2540 configuration. The mother liquor feed flow rate varied from about 9.5 to about 13.2 liters per minute, the mother liquor feed pressure varied from about 3548 to about 5701 kPa, and the concentration of N-(phosphonomethyl)glycine in the mother liquor feed varied from about 2.3 to about 3.8% by weight. The mother liquor feed temperature to the membrane separation unit was maintained at 50° C. throughout the experiment. Eleven conditions were evaluated and samples were collected at each condition once the process had stabilized for thirty minutes. The results are reported in Table 6.

TABLE 6

Design of Experiment Testing for Concentration of
Supersaturated N-(phosphonomethyl glycine) Mother Liquor by
Contact with an MPS-34 Nanofiltration Membrane in Laboratory
Evaluation System

| Feed Flow Rate (L/min) | Feed Pressure (kPa) | Feed Concentration of N-(phosphonomethyl) glycine (% by weight) | Relative Supersaturation ($\sigma$) of feed at 50° C. | Permeate Flux (Liters per m$^2$ per day) | Rejection of N-(phosophonomethyl) glycine (%) |
|---|---|---|---|---|---|
| 9.2 | 5658 | 2.35 | 0.06 | 195 | 95.7 |
| 13.1 | 5632 | 2.36 | 0.04 | 195 | 96.0 |
| 13.0 | 3588 | 2.34 | 0.06 | 90 | 93.2 |
| 9.7 | 3526 | 2.34 | 0.07 | 87 | 93.2 |
| 11.5 | 4599 | 3.14 | 0.38 | 84 | 93.7 |
| 11.5 | 4629 | 3.16 | 0.39 | 82 | 93.8 |
| 11.5 | 4629 | 3.16 | 0.38 | 83 | 93.8 |
| 9.9 | 3586 | 3.73 | 0.59 | 31 | 90.0 |
| 9.6 | 5701 | 3.74 | 0.63 | 91 | 94.2 |
| 12.9 | 3566 | 3.74 | 0.58 | 32 | 88.6 |
| 13.0 | 5687 | 3.75 | 0.60 | 92 | 94.3 |

As can be seen from Table 6, the MPS-34 nanofiltration membrane did not exhibit the same flux and rejection characteristics as the nanofiltration membrane from GE Water & Process Technologies, Inc. However, the MPS-34 membrane was operated outside of the operating pressure range specified by the manufacturer. The membrane provided adequate rejection rates when processing solids-depleted mother liquor streams with varying levels of N-(phosphonomethyl)glycine supersaturation.

Pilot-scale "static" mode experiments were conducted utilizing spiral-wound nanofiltration membranes. Static testing in the pilot-scale evaluation system was conducted using eight spiral-wound, polyamide thin-film based nanofiltration membranes with a MWCO of 250 daltons (GE Water & Process Technologies, Inc.) in the 4040 configuration oriented in series within the membrane separation unit. The average mother liquor feed temperature was 50° C., while the mother liquor feed pressure to the membrane separation unit varied from about 2534 to about 3149 kPa absolute. During static testing, the nanofiltration membranes came in contact with solids-depleted mother liquor that was unsaturated, saturated or supersaturated with N-(phosphonomethyl)glycine. The membranes had not been used to treat solids-depleted mother liquor solutions prior to the start of static testing. Mother liquor feed, retentate and permeate samples were collected from the system as the system was operated. Results are reported below in Table 7.

TABLE 7

Concentration of Supersaturated N-(phosphonomethyl) glycine Mother Liquor by Contact with Nanofiltration Membranes during Static Testing in Pilot-Scale Evaluation System

| Feed concentration of N-(phosphonomethyl) glycine (% by weight) | Relative Supersaturation ($\sigma$) of feed at 50° C. | Relative Supersaturation ($\sigma$) generated in retentate at 50° C. | Permeate to Feed ratio | Permeate Flux (Liters per m² per day) | Rejection of N-(phosphonomethyl) glycine (%) |
|---|---|---|---|---|---|
| 1.92 | −0.14 | 0.74 | 0.59 | 499 | 97.5 |
| 1.83 | −0.20 | 0.70 | 0.59 | 508 | 97.5 |
| 1.86 | −0.15 | 0.97 | 0.59 | 510 | 97.9 |
| 3.20 | 0.39 | 0.94 | 0.38 | 328 | 97.1 |
| 3.06 | 0.33 | 0.94 | 0.38 | 331 | 96.7 |

As can be seen from Table 7, the set of nanofiltration membranes could also be used to treat a solids-depleted mother liquor stream that was supersaturated with N-(phosphonomethyl)glycine. Also, the nanofiltration membranes exhibited rejection rates that were only slightly less than the rejection rates of the reverse osmosis membrane.

As can be seen with comparison to Example 1, rejection of N-(phosphonomethyl)glycine is lower when using a nanofiltration membrane as compared to a reverse osmosis membrane. Depending upon production or environmental requirements, the permeate generated from a process utilizing nanofiltration membranes could be processed further using a multi-pass design featuring a second selective membrane, preferably a reverse osmosis membrane, as shown in FIG. 5.

Example 3

Crystallization Induction Testing of Supersaturated N-(phosphonomethyl)glycine Solutions Since membrane evaluation testing was conducted using solids-depleted mother liquor solutions that were supersaturated in N-(phosphonomethyl)glycine, it was advantageous to determine the crystallization induction time for a solids-depleted mother liquor solution at given temperatures and given amounts of relative supersaturation. Solids-depleted mother liquor solutions of various degrees of relative N-(phosphonomethyl)glycine supersaturation were generated and cooled to varying temperatures with agitation. Times were recorded from the initiation of cooling until the first signs of crystallization were observed. Data is presented in Table 8.

TABLE 8

Crystallization Induction Times as a Function of N-(phosphonomethyl) glycine Supersaturation and Temperature

| Crystallization Hold Temperature (° C.) | Relative Supersaturation ($\sigma$) generated by cooling | Observed N-(phosphonomethyl)glycine Crystallization Induction Time (minutes) |
|---|---|---|
| 50 | 1.12 | 18.5 |
| 50 | 1.12 | 19.7 |

TABLE 8-continued

Crystallization Induction Times as a Function of N-(phosphonomethyl) glycine Supersaturation and Temperature

| Crystallization Hold Temperature (° C.) | Relative Supersaturation ($\sigma$) generated by cooling | Observed N-(phosphonomethyl)glycine Crystallization Induction Time (minutes) |
|---|---|---|
| 40 | 1.59 | 6.8 |
| 50 | 2.00 | 2.1 |
| 50 | 2.00 | 1.5 |

As can be seen from Table 8, the induction time necessary for spontaneous crystallization of N-(phosphonomethyl)glycine from solids-depleted mother liquor solution that is supersaturated with N-(phosphonomethyl)glycine is dependent upon the level of relative supersaturation present.

In view of the above, it will be seen that the several objects of the invention are achieved and other advantageous results attained.

As various changes could be made in the above processes without departing from the scope of the invention, it is intended that all matter contained in the above description and shown in the accompanying Figures shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A process for the preparation and recovery of an N-(phosphonomethyl)glycine product, the process comprising:
    oxidizing an N-(phosphonomethyl)iminodiacetic acid substrate in an oxidation reaction zone to produce an aqueous oxidation reaction solution comprising N-(phosphonomethyl)glycine product;
    precipitating N-(phosphonomethyl)glycine product crystals from the aqueous oxidation reaction solution to produce an aqueous product slurry comprising precipitated N-(phosphonomethyl)glycine product crystals and mother liquor saturated or supersaturated in N-(phosphonomethyl)glycine product;
    separating at least a portion of the aqueous product slurry into a solids-enriched slurry fraction comprising N-(phosphonomethyl)glycine product crystals and a solids-depleted mother liquor fraction;
    contacting the solids-depleted mother liquor fraction with a selective membrane to produce a retentate enriched in N-(phosphonomethyl)glycine product relative to the solids-depleted mother liquor fraction and a permeate depleted in N-(phosphonomethyl)glycine product relative to the solids-depleted mother liquor fraction, wherein the solids-depleted mother liquor fraction initially contacted with the selective membrane is saturated or supersaturated in N-(phosphonomethyl)glycine product; and
    precipitating N-(phosphonomethyl)glycine product crystals from the retentate.

2. The process as set forth in claim 1 wherein the solids-depleted mother liquor fraction initially contacted with the selective membrane is supersaturated in N-(phosphonomethyl)glycine product.

3. The process as set forth in claim 2 wherein the concentration of N-(phosphonomethyl)glycine product in the solids-depleted mother liquor fraction is at least about 2% by weight.

4. The process as set forth in claim 2 wherein the difference between the concentration and the saturation concentration of N-(phosphonomethyl)glycine product divided by the saturation concentration of N-(phosphonomethyl)glycine product ($\sigma$) in the solids-depleted mother liquor fraction initially contacted with the selective membrane is at least about 0.5.

5. The process as set forth in claim 2 wherein the difference between the concentration and the saturation concentration of N-(phosphonomethyl)glycine product divided by the saturation concentration of N-(phosphonomethyl)glycine product ($\sigma$) in the solids-depleted mother liquor fraction initially contacted with the selective membrane is at least about 1.

6. The process as set forth in claim 1 wherein the difference between the concentration and the saturation concentration of N-(phosphonomethyl)glycine product divided by the saturation concentration of N-(phosphonomethyl)glycine product ($\sigma$) in the solids-depleted mother liquor fraction initially contacted with the selective membrane is from about 0 to about 2.

7. The process as set forth in claim 1 wherein the difference between the concentration and the saturation concentration of N-(phosphonomethyl)glycine divided by the saturation concentration of N-(phosphonomethyl)glycine ($\sigma$) in the solids-depleted mother liquor fraction initially contacted with the selective membrane is from about 0 to about 1.5.

8. The process as set forth in claim 2 wherein the difference between the concentration and the saturation concentration of N-(phosphonomethyl)glycine product divided by the saturation concentration of N-(phosphonomethyl)glycine product ($\sigma$) in the solids-depleted mother liquor fraction initially contacted with the selective membrane is from about 1 to about 1.5.

9. The process as set forth in claim 2 wherein the solids-depleted mother liquor fraction is contacted with the selective membrane in a membrane separation unit and the residence time through the membrane separation unit is no greater than the induction time required for formation of N-(phosphonomethyl)glycine product crystals in the solids-depleted mother liquor fraction supersaturated in N-(phosphonomethyl)glycine product.

10. The process as set forth claim 2 wherein the pH of the solids-depleted mother liquor fraction contacted with the selective membrane is no greater than about 2.

11. The process as set forth in claim 2 wherein N-(phosphonomethyl)glycine product crystals are precipitated by removing water from the aqueous oxidation reaction solution to increase the concentration of N-(phosphonomethyl)glycine product in the aqueous oxidation reaction solution, precipitate N-(phosphonomethyl)glycine product crystals and form the aqueous product slurry comprising N-(phosphonomethyl)glycine product crystals and the mother liquor saturated or supersaturated in N-(phosphonomethyl)glycine.

12. The process as set forth in claim 11 wherein the aqueous oxidation reaction solution is cooled as water is evaporated from the aqueous oxidation reaction solution under substantially adiabatic conditions by reducing the pressure to thereby increase the concentration of N-(phosphonomethyl)glycine product in the aqueous oxidation reaction solution, precipitate N-(phosphonomethyl)glycine product crystals and produce the aqueous product slurry.

13. The process as set forth in claim 12 wherein the evaporation cools the aqueous oxidation reaction solution to a temperature of from about 40° C. to about 80° C. and from about 5% to about 30% by weight of the aqueous oxidation reaction solution is evaporated.

14. The process as set forth in claim 11 wherein water is evaporated from the aqueous oxidation reaction solution by heat-driven evaporative crystallization to thereby increase the concentration of N-(phosphonomethyl)glycine product in the aqueous oxidation reaction solution, precipitate N-(phosphonomethyl)glycine product crystals and produce the aqueous product slurry comprising N-(phosphonomethyl)glycine product crystals and the mother liquor saturated or supersaturated in N-(phosphonomethyl)glycine.

15. The process as set forth in any claim 2 further comprising separating N-(phosphonomethyl)glycine product crystals from the solids-enriched slurry fraction to produce an N-(phosphonomethyl)glycine wet-cake product.

16. A process for the preparation and recovery of an N-(phosphonomethyl)glycine product, the process comprising:
    oxidizing an N-(phosphonomethyl)iminodiacetic acid substrate in an oxidation reaction zone to produce an aqueous oxidation reaction solution comprising N-(phosphonomethyl)glycine product;
    precipitating N-(phosphonomethyl)glycine product crystals from the aqueous oxidation reaction solution to produce an aqueous product slurry comprising precipitated N-(phosphonomethyl)glycine product crystals and mother liquor, wherein precipitation is achieved by increasing the concentration of N-(phosphonomethyl)glycine product by removal of water from the aqueous oxidation reaction solution;
    separating at least a portion of the aqueous product slurry into a solids-enriched slurry fraction comprising N-(phosphonomethyl)glycine product crystals and a solids-depleted mother liquor fraction comprising N-(phosphonomethyl)glycine;

contacting the solids-depleted mother liquor fraction with a selective membrane to produce a retentate enriched in N-(phosphonomethyl)glycine relative to the solids-depleted mother liquor fraction and a permeate depleted in N-(phosphonomethyl)glycine relative to the solids-depleted mother liquor fraction;

precipitating N-(phosphonomethyl)glycine product crystals from the retentate.

17. The process as set forth in 16 wherein the aqueous oxidation reaction solution is cooled as water is evaporated from the aqueous oxidation reaction solution under substantially adiabatic conditions by reducing the pressure to thereby increase the concentration of N-(phosphonomethyl)glycine product in the aqueous oxidation reaction solution, precipitate N-(phosphonomethyl)glycine product crystals and produce the aqueous product slurry.

18. The process as set forth in claim 17 wherein the evaporation cools the aqueous oxidation reaction solution to a temperature of from about 40° C. to about 80° C. and from about 5% to about 30% by weight of the aqueous oxidation reaction solution is evaporated.

19. The process as set forth in 16 wherein water is evaporated from the aqueous oxidation reaction solution by heat-driven evaporative crystallization to thereby increase the concentration of N-(phosphonomethyl)glycine product in the aqueous oxidation reaction solution, precipitate N-(phosphonomethyl)glycine product crystals and produce the aqueous product slurry.

20. The process as set forth in claim 16 wherein the solids-depleted mother liquor fraction initially contacted with the selective membrane is saturated or supersaturated in N-(phosphonomethyl)glycine product.

21. The process as set forth in claim 20 wherein the solids-depleted mother liquor fraction initially contacted with the selective membrane is supersaturated in N-(phosphonomethyl)glycine product.

22. The process as set forth in claim 21 wherein the concentration of N-(phosphonomethyl)glycine product in the solids-depleted mother liquor fraction is at least about 2% by weight.

23. The process as set forth in claim 21 wherein the difference between the concentration and the saturation concentration of N-(phosphonomethyl)glycine product divided by the saturation concentration of N-(phosphonomethyl)glycine product ($\sigma$) in the solids-depleted mother liquor fraction initially contacted with the selective membrane is at least about 0.5.

24. The process as set forth in claim 21 wherein the solids-depleted mother liquor fraction is contacted with the selective membrane in a membrane separation unit and the residence time through the membrane separation unit is no greater than the induction time required for formation of N-(phosphonomethyl)glycine product crystals in the solids-depleted mother liquor fraction supersaturated in N-(phosphonomethyl)glycine product.

25. The process as set forth in claim 21 wherein the pH of the solids-depleted mother liquor fraction contacted with the selective membrane is no greater than about 2.

26. The process as set forth in claim 21 further comprising separating N-(phosphonomethyl)glycine product crystals from the solids-enriched slurry fraction to produce an N-(phosphonomethyl)glycine wet-cake product.

27. A process for the preparation and recovery of an N-(phosphonomethyl)glycine product, the process comprising:

oxidizing an N-(phosphonomethyl)iminodiacetic acid substrate in an oxidation reaction zone to produce an aqueous oxidation reaction solution comprising N-(phosphonomethyl)glycine product;

precipitating N-(phosphonomethyl)glycine product crystals from the aqueous oxidation reaction solution to produce an aqueous product slurry comprising precipitated N-(phosphonomethyl)glycine product crystals and mother liquor;

separating at least a portion of the aqueous product slurry into a solids-enriched slurry fraction comprising N-(phosphonomethyl)glycine product crystals and a solids-depleted mother liquor fraction comprising N-(phosphonomethyl)glycine;

contacting the solids-depleted mother liquor fraction with a selective membrane to produce a retentate enriched in N-(phosphonomethyl)glycine relative to the solids-depleted mother liquor fraction and a permeate depleted in N-(phosphonomethyl)glycine relative to the solids-depleted mother liquor fraction;

precipitating N-(phosphonomethyl)glycine product crystals from the retentate; and recycling at least a portion of the permeate to the oxidation reaction zone.

28. A process for recovering an N-(phosphonomethyl)glycine product from an aqueous product slurry comprising N-(phosphonomethyl)glycine product crystals and a mother liquor, the process comprising:

separating at least a portion of the aqueous product slurry into a solids-enriched slurry fraction comprising N-(phosphonomethyl)glycine product crystals and a solids-depleted mother liquor fraction comprising N-(phosphonomethyl)glycine;

separating N-(phosphonomethyl)glycine product crystals from the solids-enriched slurry fraction to produce an N-(phosphonomethyl)glycine wet-cake product;

contacting the solids-depleted mother liquor fraction with a selective membrane to produce a retentate enriched in N-(phosphonomethyl)glycine relative to the solids-depleted mother liquor fraction and a permeate depleted in N-(phosphonomethyl)glycine relative to the solids-depleted mother liquor fraction;

precipitating N-(phosphonomethyl)glycine product crystals from the retentate; and recycling and combining at least a portion of the permeate with the solids-depleted mother liquor fraction to dilute and reduce the concentration of N-(phosphonomethyl) glycine in the solids-depleted mother liquor fraction contacted with the selective membrane.

29. A process for recovery of an N-(phosphonomethyl) glycine product from an aqueous product slurry comprising N-(phosphonomethyl)glycine product crystals and a mother liquor, the process comprising:

decanting a solids-depleted mother liquor decantate comprising N-(phosphonomethyl)glycine from at least a portion of the aqueous product slurry to form a solids-enriched slurry fraction comprising N-(phosphonomethyl)glycine product crystals;

separating N-(phosphonomethyl)glycine product crystals from the solids-enriched slurry fraction to produce an N-(phosphonomethyl)glycine wet-cake product;

contacting the solids-depleted mother liquor decantate with a selective membrane to produce a retentate enriched in N-(phosphonomethyl)glycine relative to the solids-depleted mother liquor decantate and a permeate depleted in N-(phosphonomethyl)glycine relative to the solids-depleted mother liquor decantate; and precipitating N-(phosphonomethyl)glycine product crystals from the retentate.

* * * * *